(12) United States Patent
Li et al.

(10) Patent No.: US 12,270,736 B1
(45) Date of Patent: Apr. 8, 2025

(54) DGT PASSIVE SAMPLING DEVICE AND METHOD FOR WATER BODY DETECTION

(71) Applicant: Inner Mongolia University of Science and Technology, Baotou (CN)

(72) Inventors: Weiping Li, Baotou (CN); Zhi Yao, Baotou (CN); Wenhuan Yang, Baotou (CN); Junfeng Shi, Baotou (CN)

( * ) Notice: Subject to any disclaimer, the term of this patent is extended or adjusted under 35 U.S.C. 154(b) by 0 days.

(21) Appl. No.: 18/942,825

(22) Filed: Nov. 11, 2024

(30) Foreign Application Priority Data

Jun. 27, 2024 (CN) .......................... 202410843955.7

(51) Int. Cl.
*G01N 1/16* (2006.01)
*G01N 33/18* (2006.01)
*G01N 1/10* (2006.01)

(52) U.S. Cl.
CPC ........... *G01N 1/16* (2013.01); *G01N 33/1886* (2013.01); *G01N 2001/1031* (2013.01)

(58) Field of Classification Search
CPC ................. G01N 1/16; G01N 33/1886; G01N 2001/1031; G01N 1/10
USPC ............... 73/863.21, 863.23, 863.31, 864.91
See application file for complete search history.

(56) References Cited

FOREIGN PATENT DOCUMENTS

| CN | 110702855 A | 1/2020 | |
|---|---|---|---|
| CN | 111060424 A | 4/2020 | |
| CN | 112033755 A | 12/2020 | |
| CN | 113607605 A | * 11/2021 | ............... G01N 1/10 |
| CN | 218055527 U | 12/2022 | |
| CN | 116718516 A | 9/2023 | |
| CN | 117907158 A | 4/2024 | |
| CN | 221078162 U | 6/2024 | |

* cited by examiner

*Primary Examiner* — Robert R Raevis

(57) ABSTRACT

A DGT passive sampling device for water body detection includes a bottom fixed unit, where the bottom fixed unit includes an inserting drill bit; a passive sampling unit arranged at the top of the bottom fixed unit; and a floating marking unit arranged at the top of the passive sampling unit, where the floating marking unit includes a winding cylinder I, and the winding cylinder I is movably connected to the chassis by control inner ropes. After the inserting drill bit is inserted into the underwater soils, the bottom cavity winding source is started, the rotation of the bottom cavity roll releases the downward movement of the middle ropes, so that the passive sampling unit falls, while the bottom cavity roll may make the passive sampling unit regularly distributed at different heights of the water bottom by releasing different lengths of the middle ropes.

14 Claims, 14 Drawing Sheets

DGT PASSIVE SAMPLING DEVICE AND METHOD FOR WATER BODY DETECTION

CROSS-REFERENCE TO THE RELATED APPLICATIONS

This application is based upon and claims priority to Chinese Patent Application No. 202410843955.7, filed on Jun. 27, 2024, the entire contents of which are incorporated herein by reference.

TECHNICAL FIELD

The present disclosure relates to the technical field of sampling, and in particular, to a diffusive gradients in thin-films (DGT) passive sampling device and a method for water body detection.

BACKGROUND

DGT, also known as diffuse gradient film technology, is a passive sampling technique that is widely used in environmental science, especially for the determination of dissolved pollutants (such as heavy metals and nutrients) in water. DGT technology collects and concentrates pollutants by simulating the natural diffusion process of pollutants in water bodies, thereby providing information on the time-weighted average concentration of pollutants.

Chinese patent CN202410116509.6 published a DGT device, including an adsorption membrane, a diffusion membrane, a filter membrane and a DGT shell, and: preparing the diffusion membrane with 2% agarose solution; a certain amount of XAD18 resin was dried, ground and activated, and then put into 2% agarose solution to make the adsorption film; and polytetrafluoroethylene (PTFE), polyvinylidene fluoride (PVDF), hydrophilic nylon (NL) and polyethersulfone (PES) membranes were screened, finally, PTFE with the least adsorption of polycyclic aromatic hydrocarbon derivatives was selected as the DGT membrane. The passive sampling technology of polycyclic aromatic hydrocarbon derivatives proposed by the above invention solved the problems of large detection error, cumbersome pretreatment and inability to reflect the true level of pollutants in a certain period of time caused by active sampling.

Chinese patent CN201910984388.6 published a combined device and method for passive sampling of in-situ biological exposure in a water environment, the device included an exposure device for aquatic organisms, an exposure device for epifauna and benthos, a passive sampler for a water body, a passive sampler for multi-section pore water, a passive sampler for sediment water interface flux, and a floating ball. The biological exposure device of the above invention included an exposure device for aquatic organisms and an exposure device for epifauna and benthos, the tested organisms included those living in the upper water, the bottom surface and the benthic, corresponding to different spatial distributions, the exposure concentration and biological effect information of pollutants in water, sediment and interface can be obtained, the height of the exposure device for aquatic organisms and the passive sampler for water body from the water surface can be adjusted, which can correspond to the change of the water level, and is suitable for tidal rivers or lakes with large water level changes.

The above-mentioned patents and the prior art have the following problems:

the existing DGT sampling device can not eliminate the influence of water flow and water microorganisms on the sampling device in water sampling, thereby affecting the stability of the sampling device and making it easy for water microorganisms to attach to the surface of the sampling device to form biofilm, and when the DGT sampling device is used to sample the water body at different heights, the adsorption layer cannot be replaced in time, so that the water pollution at different heights is attached to the same adsorption layer, which affects the subsequent analysis results of water body sampling.

SUMMARY

A purpose of this section is to outline some aspects of embodiments of the present disclosure and briefly introduce some preferred embodiments. Some simplifications or omissions may be made in this section and in the abstract of the specification and the name of the present disclosure to avoid blurring the purpose of this section, the abstract of the specification and the name of the present disclosure, however, such simplifications or omissions may not be used to limit the scope of the present disclosure.

In order to solve the above technical problems, the present disclosure provides the following technical solutions.

A DGT passive sampling device for water body detection includes:

- a bottom fixed unit, the bottom fixed unit includes an inserting drill bit arranged at the bottom of the bottom fixed unit, and the inserting drill bit is fixed at the center of the bottom of a chassis;
- a passive sampling unit, the passive sampling unit is arranged at the top of the bottom fixed unit, the passive sampling unit includes ring plates and filtering surfaces, the ring plates are arranged at the top of the bottom fixed unit, a circumferential direction of the ring plates is arranged with several filtering surfaces, an inner side of the filtering surfaces is arranged with a diffusion layer plate and an adsorption part, a counterweight sealing plate is arranged between the filtering surface and the diffusion layer plate, the counterweight sealing plate is movably connected to a bottom loose plate by a bottom vertical rod, the bottom loose plate is movably connected to a connecting cavity by a vertical plunger, and the bottom loose plate controls sliding of a hollow moving frame by an untied and guyed rope; and
- a floating marking unit, the floating marking unit is arranged at the top of the passive sampling unit, the floating marking unit includes a winding cylinder I arranged at the top of the passive sampling unit, the winding cylinder I is movably connected to the chassis by control inner ropes, the bottom of the floating marking unit is arranged with a bottom ring cavity, the interior of the bottom ring cavity is arranged with a bottom cavity winding source, and the bottom cavity winding source is movably connected to the passive sampling unit by a middle rope on the surface of a bottom cavity roll.

As a preferred solution for the DGT passive sampling device for water body detection described in the present disclosure, wherein: the chassis also includes opening sleeves, a circumferential direction of the top surface of the chassis is arranged with several opening sleeves, the interior of the opening sleeve is fixedly connected to a counterweight block by bolts, the middle part of the top surface of the chassis is fixedly connected with a sealing cavity, the interior of the sealing cavity is fixedly connected to a fixed driving source, an output shaft of the fixed driving source runs through the chassis and is movably connected to unfolding components; and the interior of the inserting drill bit is arranged with a cavity, and the lateral part of the inserting drill bit is arranged with a side groove, the output shaft of the fixed driving source is movably connected to the side groove by the middle part of the unfolding components, and a circumferential direction of the top surface of the chassis is fixedly connected to several control inner ropes and control outer ropes.

As a preferred solution for the DGT passive sampling device for water body detection described in the present disclosure, wherein: the floating marking unit also includes a floating ring, the middle of the floating ring is arranged with a power top cavity, and the power top cavity is fixedly connected to the bottom ring cavity by the floating ring; and the internal center of the power top cavity is fixedly connected to a power winding source, an output shaft of the power winding source is fixedly connected to a main drive gear, the lateral part of the main drive gear is engaged with a winding gear I, the winding gear I drives the winding cylinder I to rotatably connect to the bottom of the power top cavity through a rotating shaft at the center of the winding cylinder I, and the surface of the winding cylinder I is movably wound with control inner ropes.

As a preferred solution for the DGT passive sampling device for water body detection described in the present disclosure, wherein: the lateral part of the winding gear I is engaged with a winding gear II, the winding gear II is rotatably connected to a winding cylinder II by a rotating shaft at the center of the winding cylinder II, the winding cylinder II is rotatably connected to the bottom surface of the power top cavity by a rotating shaft, the surface of the winding cylinder II is wound with a lifting rope, and the lifting rope runs through the power top cavity and is movably connected to a squeezing block; and the outer side of the bottom ring cavity is fixedly connected to a lower extension rod and a storage rack, the inner side of the storage rack is arranged with several opening cylinders along a height direction of the storage rack, the interior of the opening cylinders is fixedly arranged with elastic elements II, the opening cylinders are elastically connected to round blocks by the elastic elements II, and the round blocks are movably connected to counterweight rings by insert plates.

As a preferred solution for the DGT passive sampling device for water body detection described in the present disclosure, wherein: the middle of the insert plates is arranged with middle grooves, the interior of the middle grooves is movably arranged with the lower extension rod, the squeezing block and the lifting rope, and the squeezing block is slidingly connected to the surface of the lower extension rod;

the interior of the bottom ring cavity is fixedly connected to a bottom cavity vertical frame, the middle part of the bottom cavity vertical frame is rotatably connected to a bottom cavity roll by a rotating shaft, and the bottom cavity roll is rotatably connected to the bottom cavity winding source by a bottom cavity roll of the bottom cavity roll; and the bottom of the bottom ring cavity is movably connected to the control outer ropes, and the surface of the control outer ropes is distributed with several counterweight rings.

As a preferred solution for the DGT passive sampling device for water body detection described in the present disclosure, wherein: the middle rope runs through the bottom ring cavity and is movably connected to a middle block, the middle block is arranged in the middle of the ring plate, the outer side of the middle block is fixedly connected to the connecting cavity, the bottom of the filtering surfaces is horizontally arranged with transverse trough stripes, the interior of the transverse trough stripe is movably arranged with a vertical weight plate, the top of the vertical weight plate is obliquely arranged with a shovel plate, the shovel plate and the filtering surfaces are movably connected, the lateral part of the vertical weight plate is fixedly connected to a side plate, and the top of the side plate is fixedly connected with a pulling rope; and the surface of the filtering surfaces is fixedly arranged with through blocks, the top of the connecting cavity is fixedly arranged with a top vertical cavity, the interior of the top vertical cavity is movably connected to the counterweight sealing plate, the pulling rope passes through the through blocks and the top vertical cavity and is movably connected to the bottom of the counterweight sealing plate, the counterweight sealing plate runs through the top vertical cavity, a lateral cavity, and an eyeplate by a top pulling rope on the top of the counterweight sealing plate, then the counterweight sealing plate is movably wound to the surface of a rotating roller, and the rotating roller is transmissibly connected to a rotating driving source through a rotating shaft in the middle of the rotating roller.

As a preferred solution for the DGT passive sampling device for water body detection described in the present disclosure, wherein: the part at the bottom of the connecting cavity corresponding to the counterweight sealing plate is arranged with an insert cavity, the lateral part of the insert cavity is fixedly connected to a side baffle, the lateral part of the side baffle is fixedly arranged with the diffusion layer plate, the bottom of the connecting cavity is fixedly connected to a liquid storage cavity, the interior of the liquid storage cavity is vertically fixed with a drawbar, the bottom of the counterweight sealing plate is fixedly connected to the bottom vertical rod, the bottom vertical rod runs through the insert cavity and is movably connected to the bottom loose plate, and the bottom loose plate is movably arranged on the surface of the drawbar; and the bottom surface of the connecting cavity is provided with through holes, the interior of the through holes is movably connected to the vertical plunger, and the vertical plunger is fixedly connected to the surface of the bottom loose plate.

As a preferred solution for the DGT passive sampling device for water body detection described in the present disclosure, wherein: the top surface of the bottom loose plate is fixedly connected to the untied and guyed rope, the untied and guyed rope runs through the connecting cavity and is movably connected to a transverse plate, the transverse plate is fixedly connected to the hollow moving frame, the inner wall of the connecting cavity is transversely arranged with a side shift groove, the hollow moving frame is slidingly connected to the side shift groove by a side block, hollow fixed frames are arranged on the left and right sides of the side shift groove, and the hollow fixed frames are fixedly connected to the inner wall of the connecting cavity; and an elastic element I is arranged between the left-side hollow fixed frame and the hollow moving frame, a top notch and a bottom notch are respectively arranged at the upper part and the lower part of the connecting cavity corresponding to the hollow moving frame, and the adsorption part is movably arranged between the hollow moving frame and the right-side hollow in fixed frame.

As a preferred solution for the DGT passive sampling device for water body detection described in the present disclosure, wherein: a bottom roll cavity is arranged at the bottom of the connecting cavity, the bottom roll cavity is rotatably connected to an output roll by an output vertical frame, and the surface of the output roll is movably wound with the adsorption part;

the top of the connecting cavity is fixedly connected with a top roll cavity, the top roll cavity is rotatably connected to a top cavity roll by a top cavity vertical frame, and the top cavity roll passes through the top cavity vertical frame by a rotating shaft in the middle of the top cavity roll and is transmissibly connected to a roll driving source; and the adsorption part includes adsorption layers and plastic film, the adsorption layers are arranged in the middle of the plastic film, and the plastic film is arranged between the adjacent adsorption layers, and the area of the plastic film between the adjacent adsorption layers is larger than the area of the adsorption layers.

Another purpose of the present disclosure is to provide a DGT passive sampling method for water body detection in view of the shortcomings of the prior art, including the following steps:

step 1: lowering and fixing: by lowering a bottom fixed unit down, making an inserting drill bit contact with underwater soils, and limiting movement of a chassis by pulling a floating marking unit through control inner ropes;

step 2: sealing and drainage: lowering a passive sampling unit in the water bodies between the bottom fixed unit and a floating marking unit, making the passive sampling unit filter and sample water bodies by filtering surfaces, during the conversion sampling at different heights, a counterweight sealing plate seals the filtering surfaces, and opening through holes at the bottom surface of a connecting cavity, to make the sampling water inside the connecting cavity be discharged into the interior of a liquid storage cavity; and step 3: removing biofilm: when the counterweight sealing plate moves down, a shovel plate may be pulled up by a pulling rope, making the shovel plate clean up the surface of the filtering surfaces, while after the filtering surface is cleaned and the counterweight sealing plate is reset and unsealed, making the water bodies continue to be sampled through the filtering surfaces.

The Beneficial Effects of the Present Disclosure are

1. By placing the floating marking unit on the water surface, the buoyancy of the floating ring suspends the floating marking unit to the water surface, and then the power winding source is operated to start, the power winding source drives the winding gear I to rotate through the main drive gear on the top of the power winding source, the winding cylinder I at the bottom of the winding gear I rotates with the winding gear I, the control inner rope on the surface of the winding cylinder I is loosened, so that the chassis at the bottom of the control inner ropes drops to the bottom of the water, and finally, the inserting drill bit at the bottom of the chassis is inserted into the underwater soils under the weight of the counterweight block, while the inserting drill bit is arranged in the middle of the bottom of the chassis and the inserting drill bit is arranged independently at the bottom of the chassis, thereby facilitating a smaller contact area between the inserting drill bit and the underwater soils, so as to reduce the influence of underwater topography on the inserting drill bit and the chassis, so that the inserting drill bit is more stable into the underwater soils.

2. The counterweight block arranged on the outer side of the top surface of the chassis can aggravate the chassis, so that the chassis is more stable under the counterweight of the counterweight block, thereby making the counterweight block and the chassis move down in the water under the action of gravity; and while when the inserting drill bit is inserted into the underwater soils, the fixed driving source is started at intervals, the output shaft of the fixed driving source drives the unfolding component to move outward, the unfolding component is inserted into the underwater soils, so that the inserting drill bit is constrained inside the soils, thus completing the bottom anchoring of the device and improving the overall stability of the sampling device.

3. When the winding gear I rotates, under the coordination of tooth ratio, the winding gear I may drive the winding gear II to rotate, making the winding cylinder II drive the lifting rope on the surface of the winding cylinder II to shrink, thereby causing the lifting rope to pull the squeezing block at the bottom of the lifting rope up along the lower extension rod, so that the squeezing block may make contact with the middle grooves inside the insert plates of different heights during the upward movement, thus, when the squeezing block moves in the middle grooves, the squeezing block squeezes the insert plates and the round blocks to move towards the interior of the opening cylinder, the elastic elements II are squeezed, when the insert plates move towards the interior of the opening cylinder, the restriction on the counterweight rings at the top of the insert plates is removed, so that the counterweight rings decrease in their own weight traction, while in the falling of the counterweight rings, the control outer ropes are stretched, so that several counterweight rings are distributed at different heights at the bottom of the water, thereby making the counterweight rings pull the floating marking unit by the control outer ropes; and the counterweight rings of different heights are arranged on the outside of the control inner ropes, thereby reducing the instability caused by the long distance between the bottom fixed unit and the floating marking unit.

4. After the inserting drill bit is inserted into the underwater soils, the bottom cavity winding source is started, so that the bottom cavity winding source drives the bottom cavity roll to rotate, the rotation of the bottom cavity roll releases the downward movement of the middle ropes, so that the passive sampling unit falls, while the bottom cavity roll may make the passive sampling unit regularly distributed at different heights of the water bottom by releasing different lengths of the middle ropes, so that the passive sampling unit may sample the water layer at different heights.

5. When the passive sampling unit samples the water layers, the filtering surfaces distributed at different directions of the floating marking unit may make filtered water pass through the diffusion layer board on the back, then the filtered water is adsorbed into the adsorption layer on the surface of the adsorption part between the hollow fixed frame and the hollow moving frame, while when timing samplings of the passive sampling unit are completed, the middle ropes continue to be released, so that the passive sampling unit continues to move down, when the passive sampling unit moves down to the next sampling point, the rotating driving source rotates, the rotating roll rotates, making the top pulling rope on the surface of the rotating roller be released, thereby making the counterweight sealing plate constrained by the top pulling rope be released from the interior of the top vertical cavity and eventually fall into the interior of the insert cavity; the filtering surfaces are sealed and blocked and the falling of the counterweight seal plate may pull the pulling rope to contract, thereby making the vertical weight plate and the shovel plate with a weight less than the counterweight sealing plate raise, so that the shovel plate lifts up the surface of the filtering surfaces, and the biofilm on the surface of the filtering surfaces is removed.

6. In the downward movement of the counterweight sealing plate, the counterweight sealing plate squeezes the bottom loose plate down through the bottom vertical rod, so that the bottom loose plate moves down and moves along the vertical plunger, so that the vertical plunger is pulled out from the bottom of the connecting cavity, the through holes on the bottom surface of the connecting cavity sealed by the vertical plunger are opened, the water at the interior of the connecting cavity is discharged into the interior of the liquid storage cavity through the through holes, thereby increasing the weight of the passive sampling unit, and thereby reducing the accidental shaking of the passive sampling unit caused by the impact of water flow in the water flow, and meanwhile, it also facilitates reducing the impact of water samples of different heights on the adsorption layers in subsequent sampling.

7. The moving down of the bottom loose plate may also pull the untied and guyed rope down, the untied and guyed rope pulls the transverse plate and the hollow fixed frame to close to the diffusion layer plate, so that the hollow moving frame releases the clamping of the adsorption part under the elastic push of the elastic element I and the closure of the hollow fixed frame. It should be noted that the hollow moving frame may move between the top notch and the bottom notch when the hollow moving frame cooperates with the hollow fixed frame to clamp the adsorption part under the elastic push of the elastic element I, to seal the top notch and the bottom notch.

8. After the hollow moving frame releases the clamping of the adsorption part, the roll driving source rotates to drive the top cavity roll to contract, so that the adsorption part is rolled to the surface of the top cavity roll, so that the adsorption layers on the surface of the adsorption part between the hollow fixed frame and the hollow moving frame are rolled up to the surface of the top cavity roll, the adsorption layers below the adsorption layers that are not transferred to the interior of the connecting cavity are transferred between the hollow fixed frame and the hollow moving frame, at this time, after the rotating driving source is reversed, the counterweight sealing plate makes the rotating driving source roll the pulling rope through the rotating roller, the counterweight sealing plate is rolled up to the interior of the top vertical cavity, at this time, the drawbar is lifted up to seal the through holes on the bottom surface of the connecting cavity, the bottom loose plate relieves the tension of the untied and guyed rope, the hollow moving frame is driven by the elasticity of the elastic element I, the hollow moving frame and the hollow fixed frame clamp the adsorption part, the unused adsorption layers on the surface of the adsorption part are arranged in the middle of the hollow moving frame, the adsorption layers continue to sample the next sampling height, thereby completing the sampling of water bodies at different heights.

9. While the reset of the counterweight sealing plate may release the pulling on the pulling rope, so that the vertical weight plate may move downwards and reset under the action of gravity, however, the plastic film arranged between the adjacent adsorption layers may be in the roll of the top cavity roll, making the plastic film may be rolled to the surface of the top cavity roll, and the plastic film rolled onto the surface of the top cavity roll separates the sample that has been adsorbed, reducing the mutual influence between multiple sampling adsorption layers.

BRIEF DESCRIPTION OF THE DRAWINGS

In order to more clearly explain the technical solutions of embodiments of the present disclosure, the following will briefly introduce the accompanying drawings used in the description of the embodiments, wherein.

Figure 1:
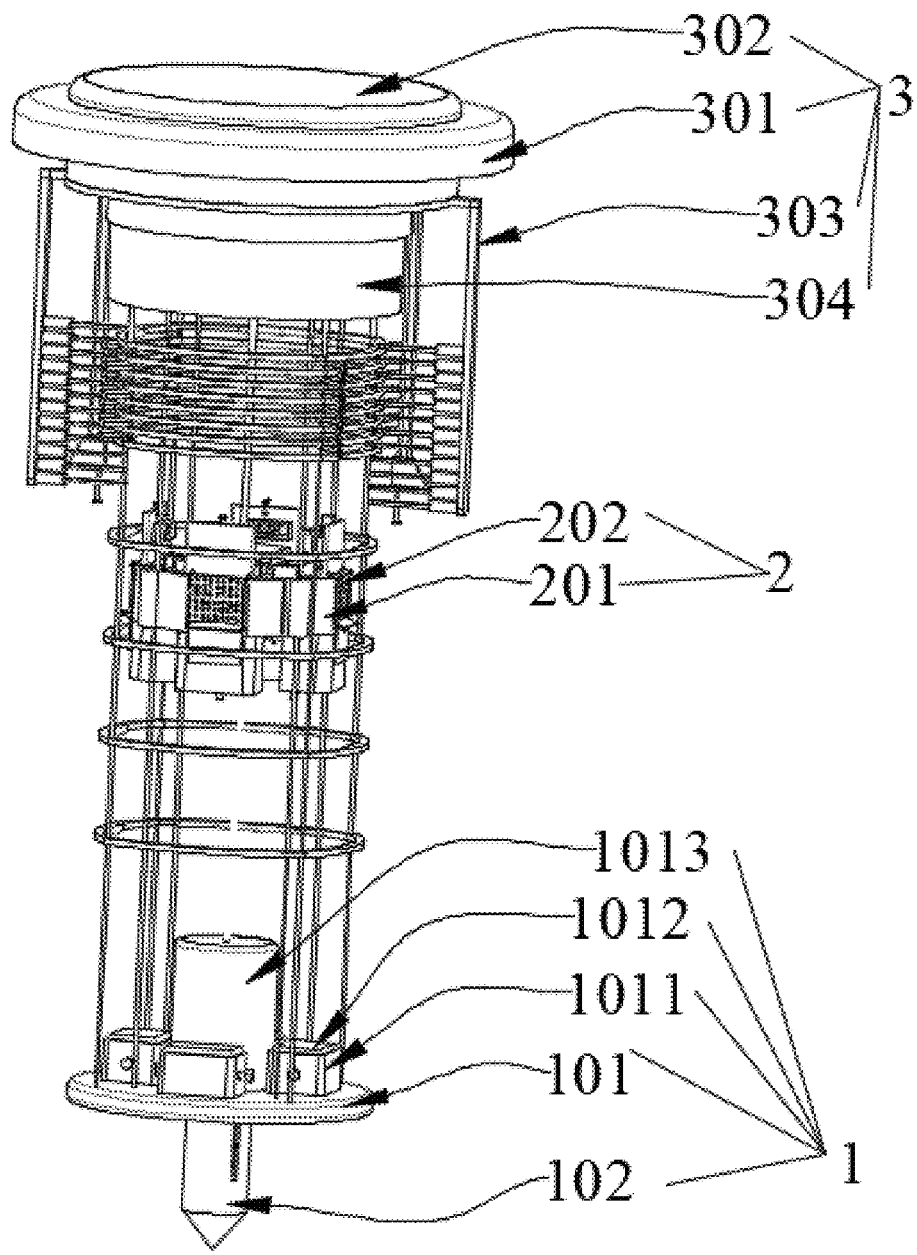
FIG. 1 is an overall structure schematic diagram of the present disclosure.
Figure 2:
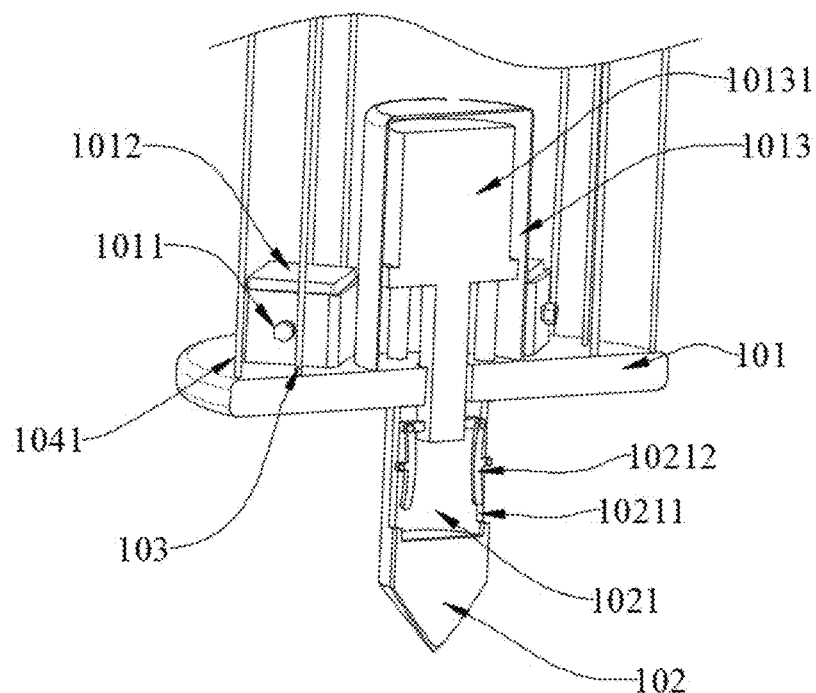
FIG. 2 is a structure connection schematic diagram of a bottom fixed unit of the present disclosure.
Figure 3:
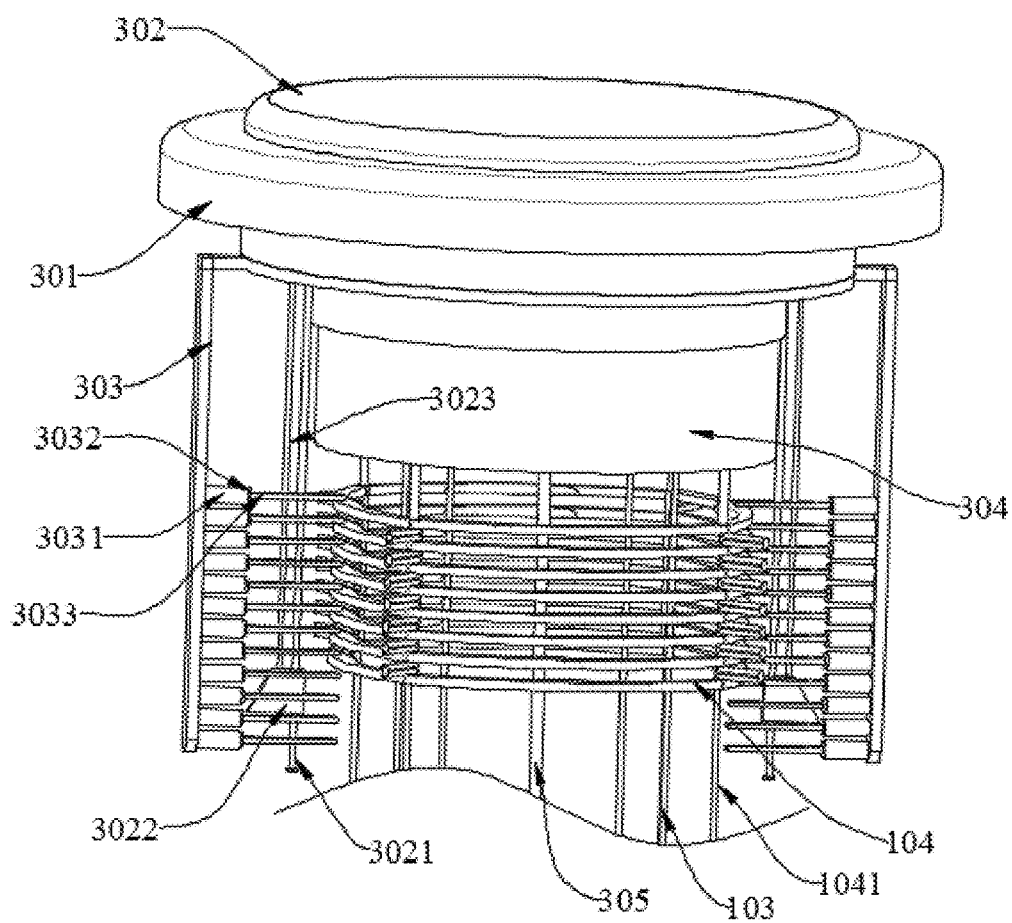
FIG. 3 is a structure connection schematic diagram of a floating marking unit of the present disclosure.
Figure 4:
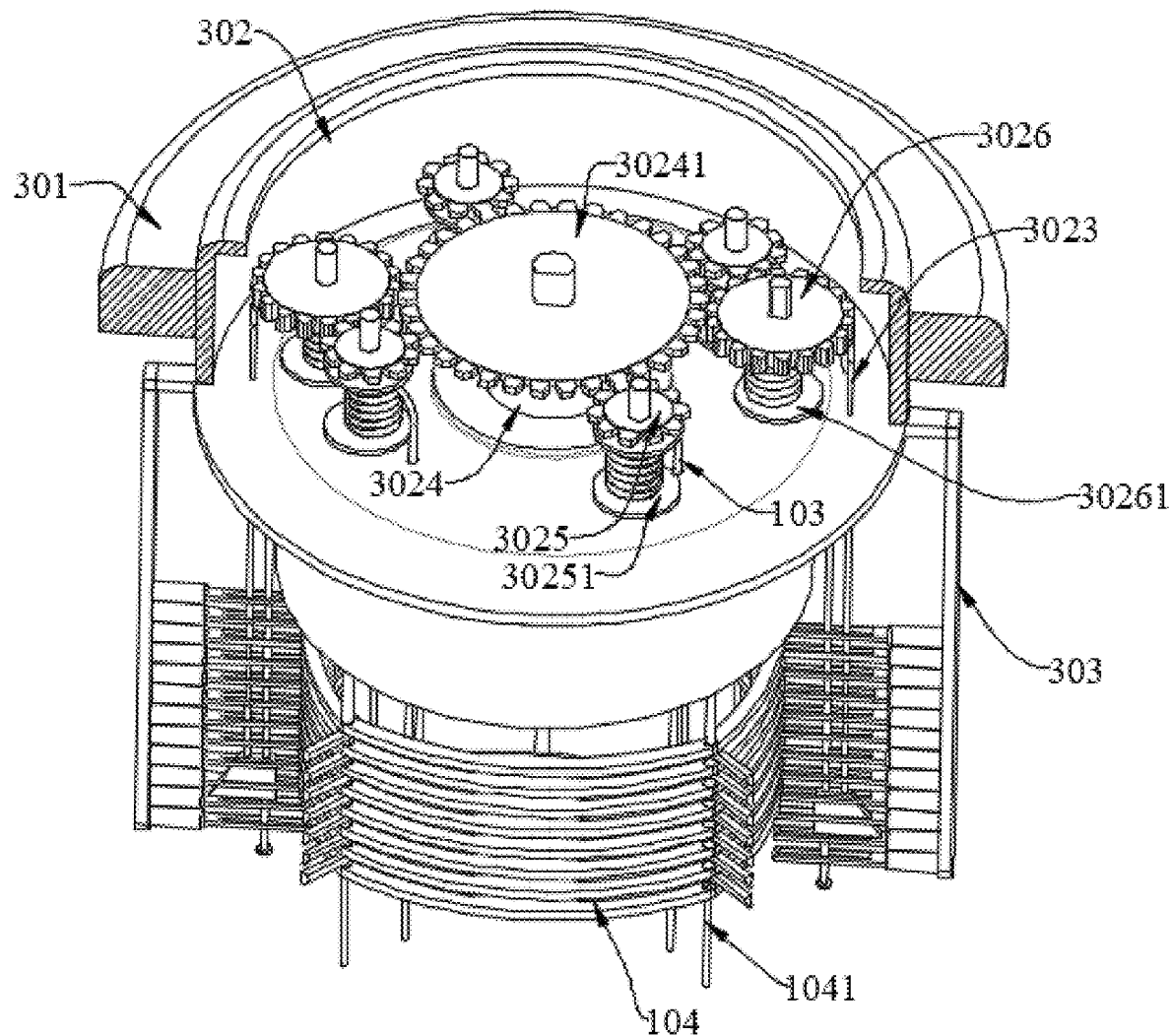
FIG. 4 is an internal structural connection schematic diagram of a power top cavity of the present disclosure.
Figure 5:
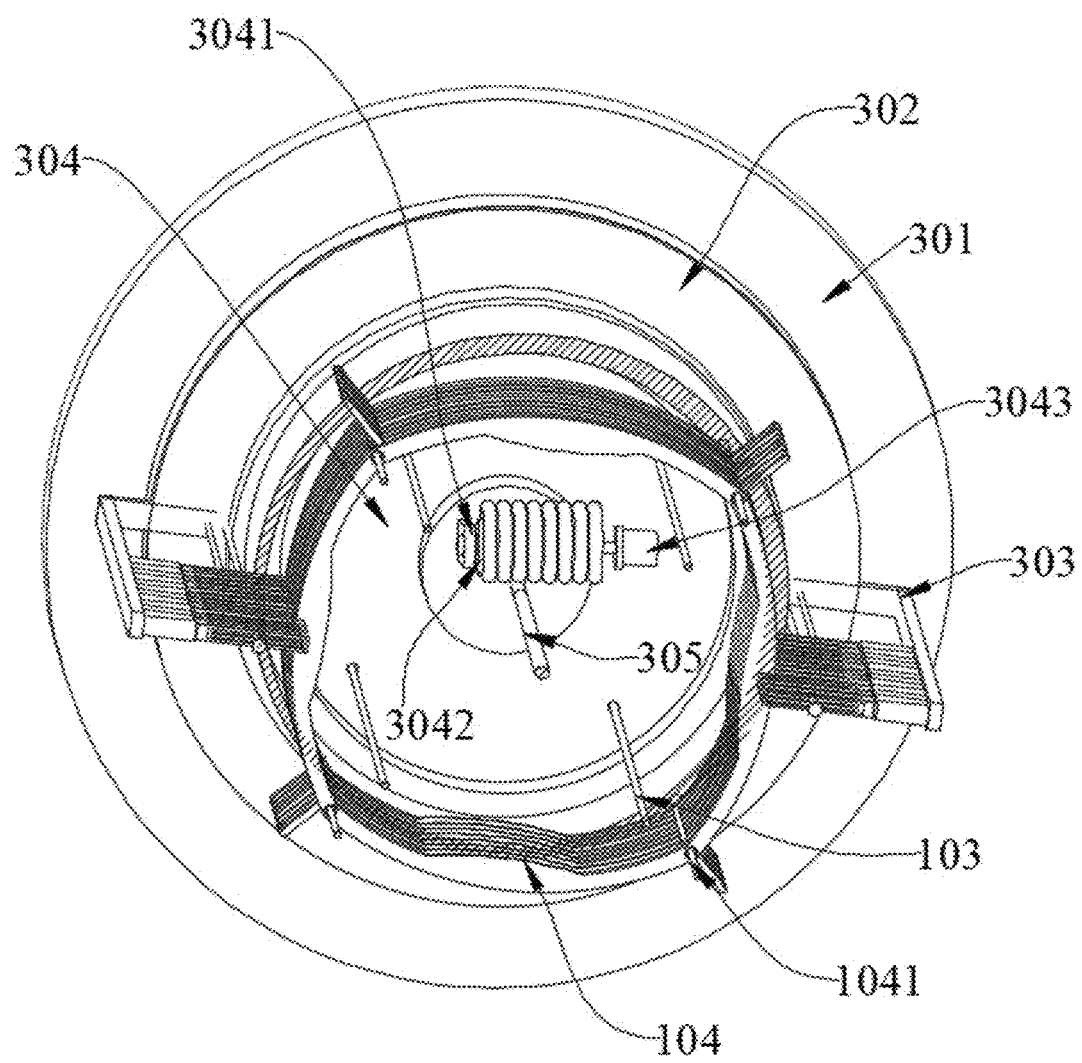
FIG. 5 is an internal structural connection schematic diagram of a bottom ring cavity of the present disclosure.
Figure 6:
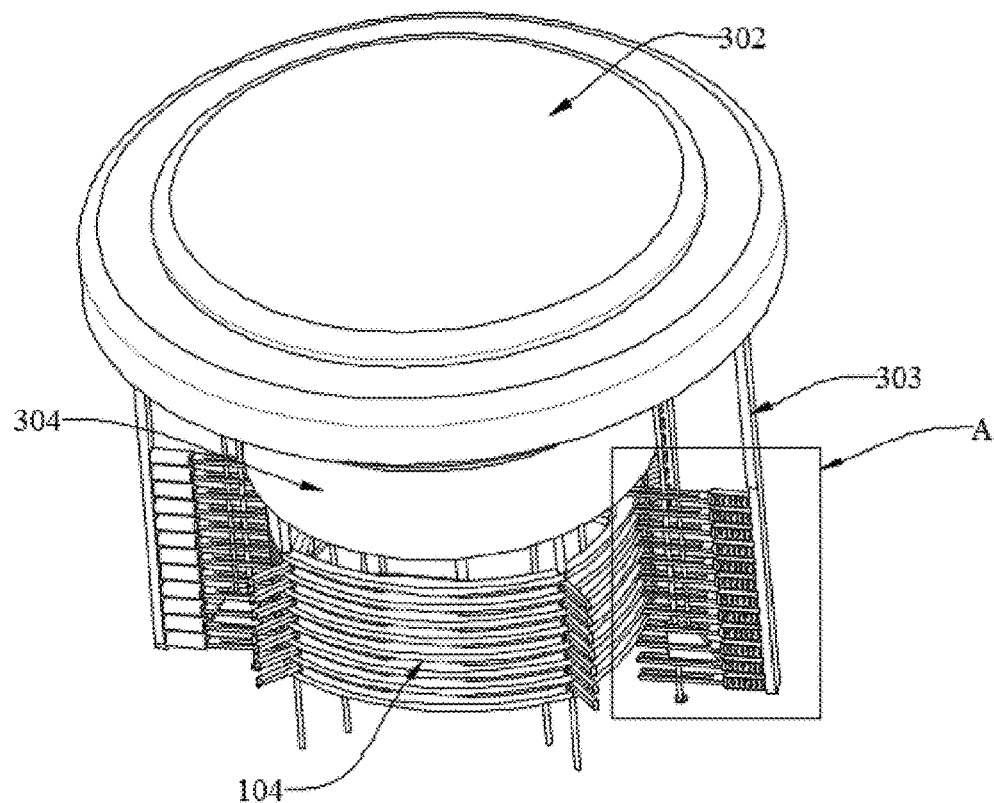
FIG. 6 is a structure connection schematic diagram of a storage rack of the present disclosure.
Figure 7:
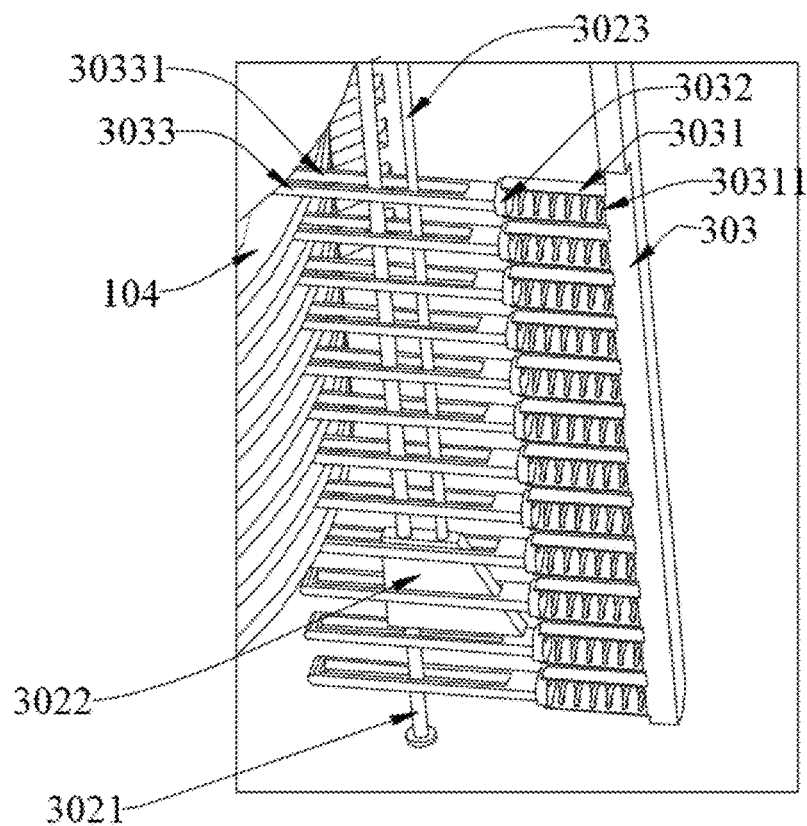
FIG. 7 shows an enlarged structure schematic diagram of part A in FIG. 6.
Figure 8:
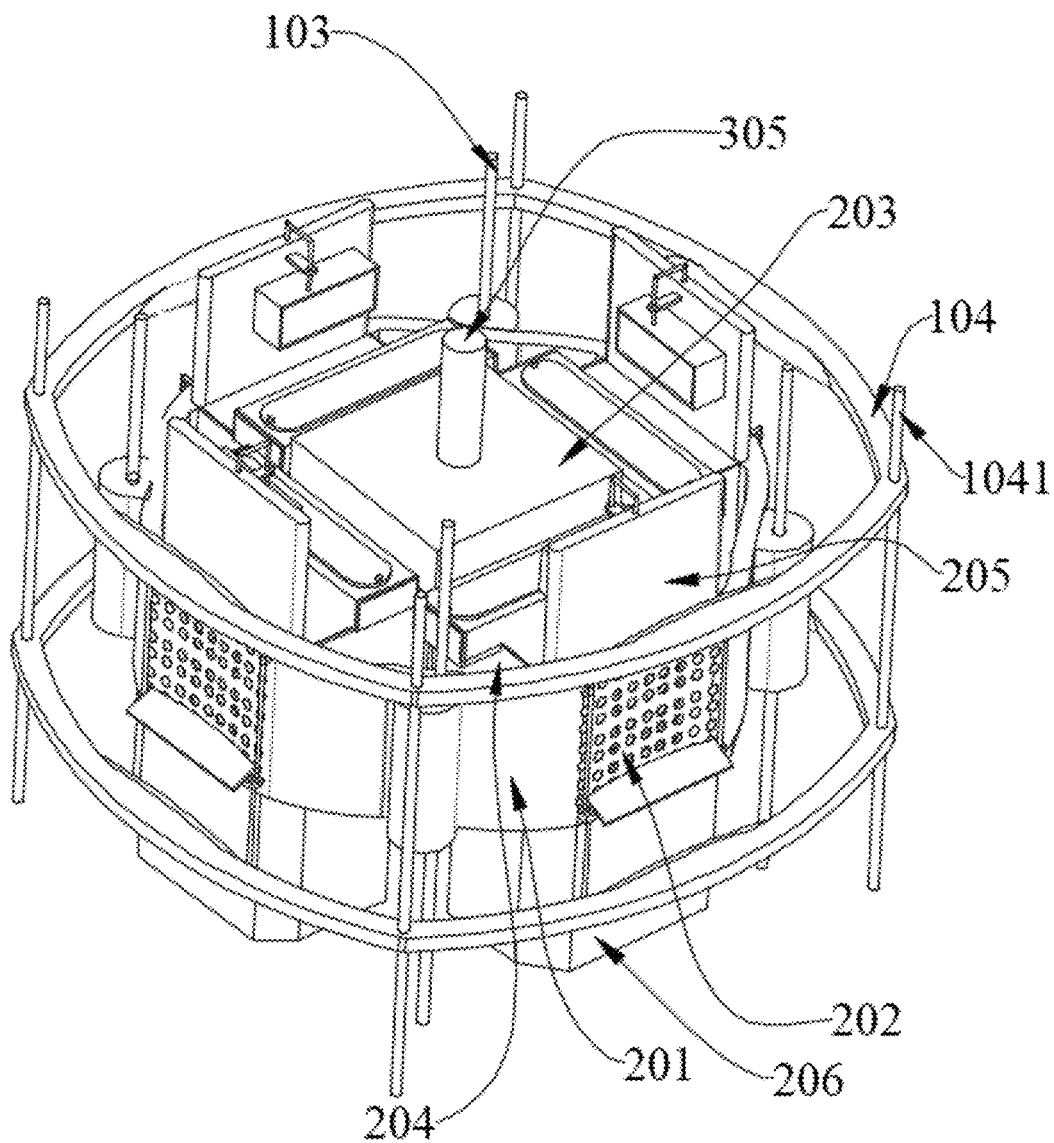
FIG. 8 is a structure connection schematic diagram of a passive sampling unit of the present disclosure.
Figure 9:
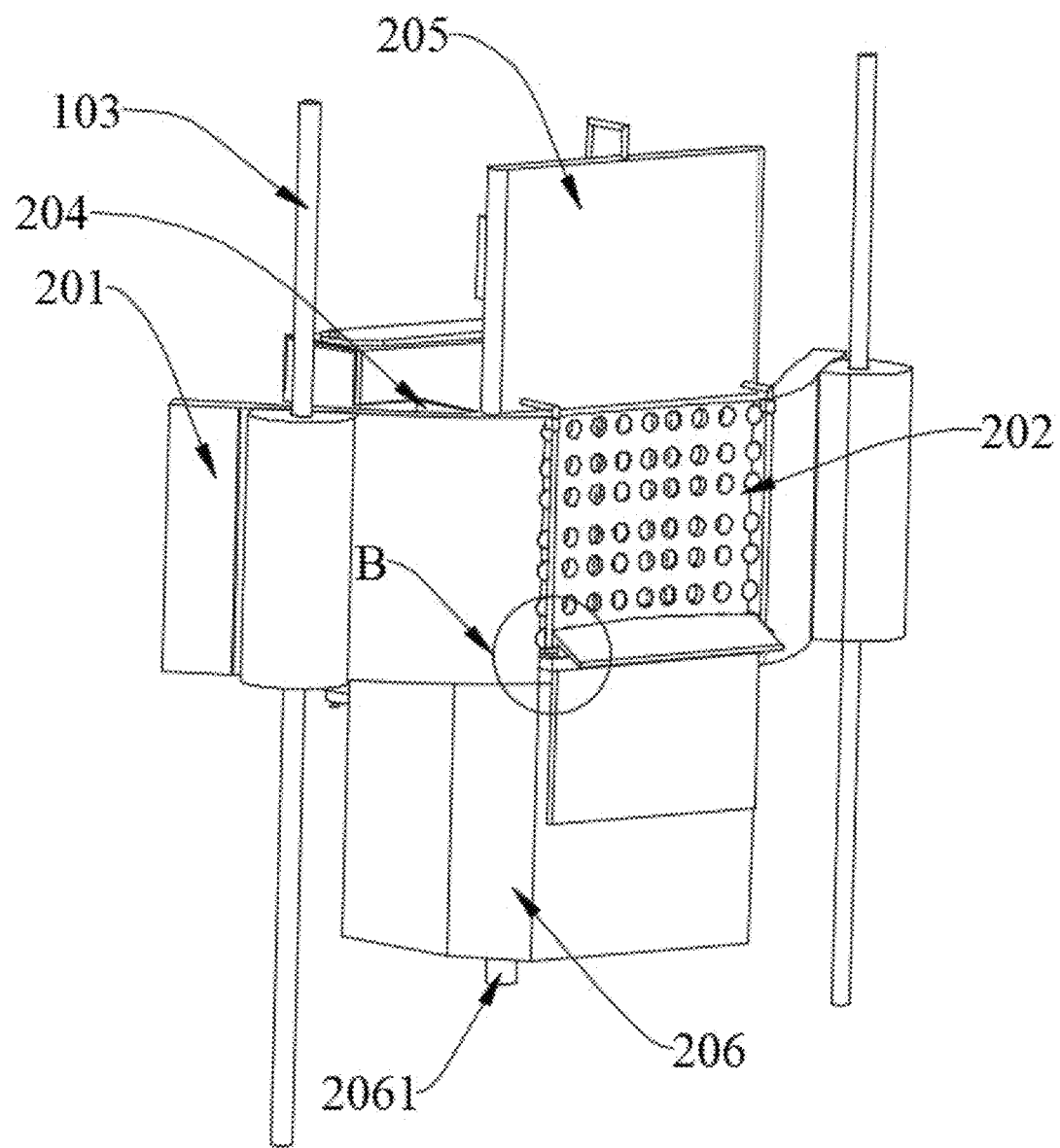
FIG. 9 is a connection schematic diagram of a filtering surface, a top vertical cavity and a liquid storage cavity of the present disclosure.
Figure 10:
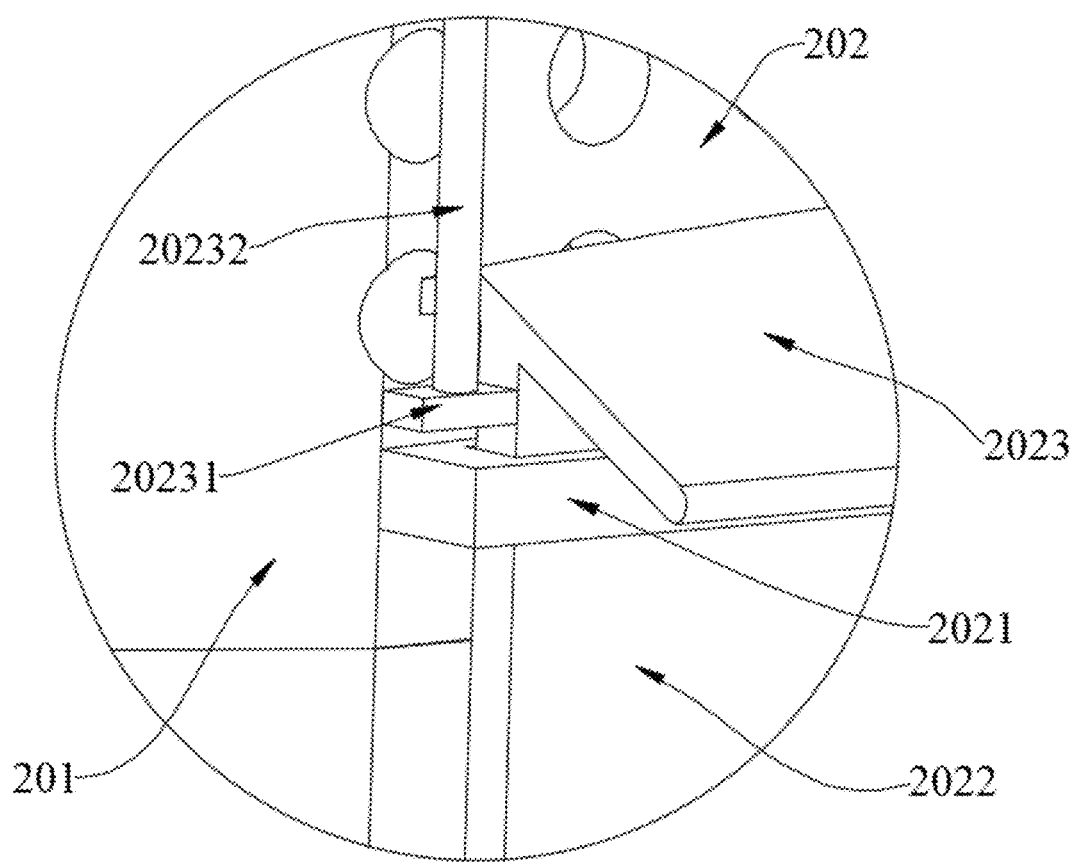
FIG. 10 shows an enlarged structure schematic diagram of part B in FIG. 9.
Figure 11:
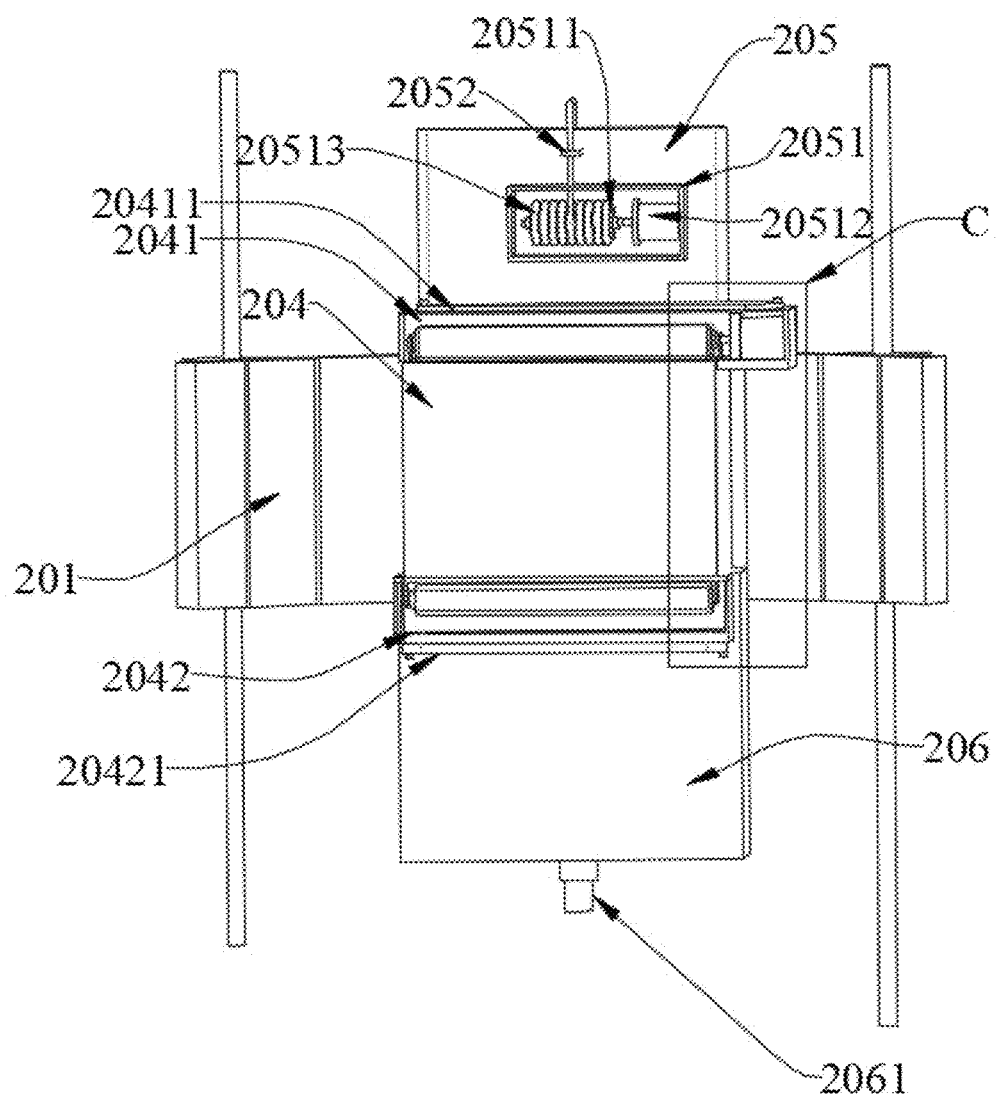
FIG. 11 is an internal schematic diagram of a lateral cavity, a top roll cavity and a bottom roll cavity of the present disclosure.
Figure 12:
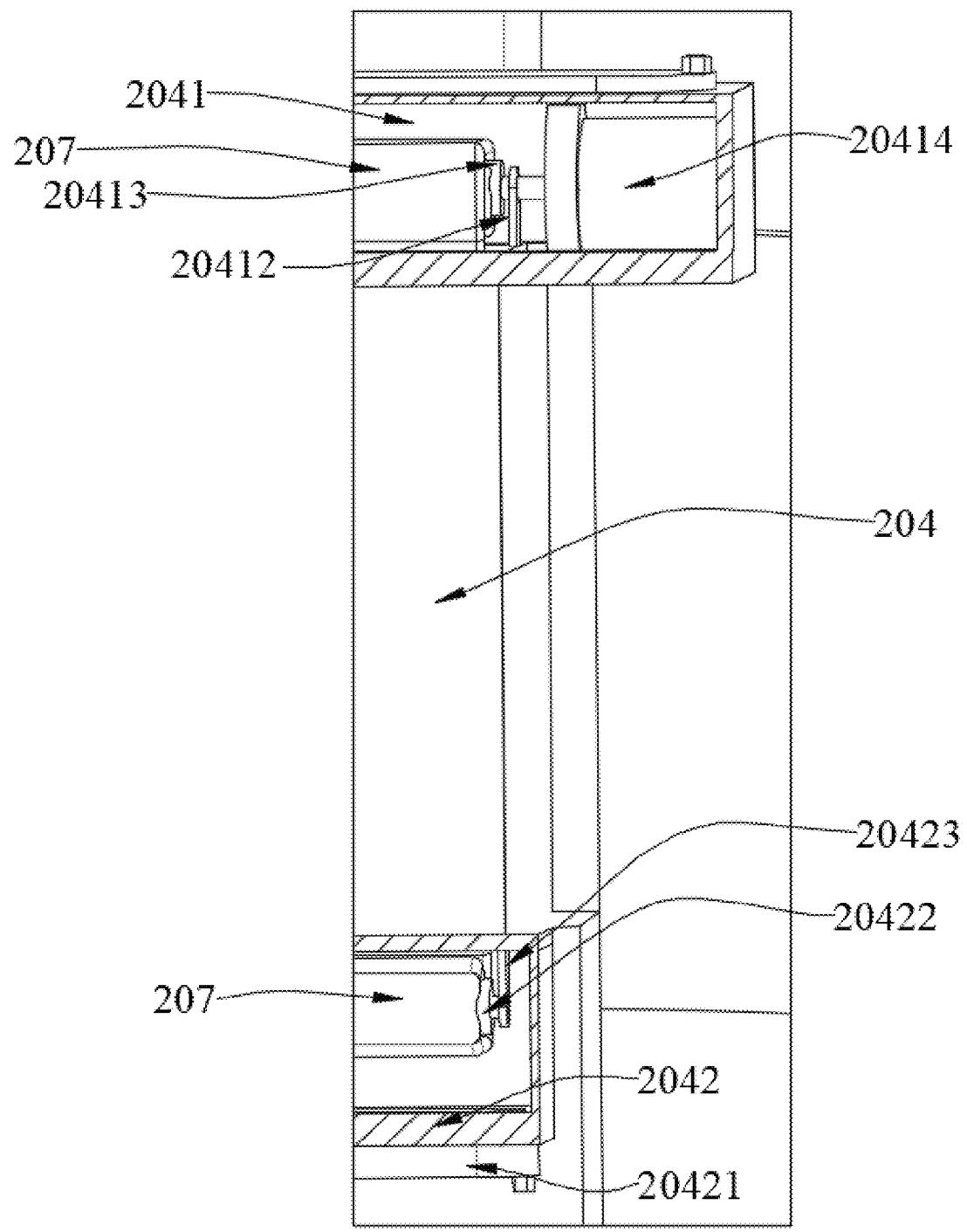
FIG. 12 shows an enlarged structure schematic diagram of part C in FIG. 11.
Figure 13:
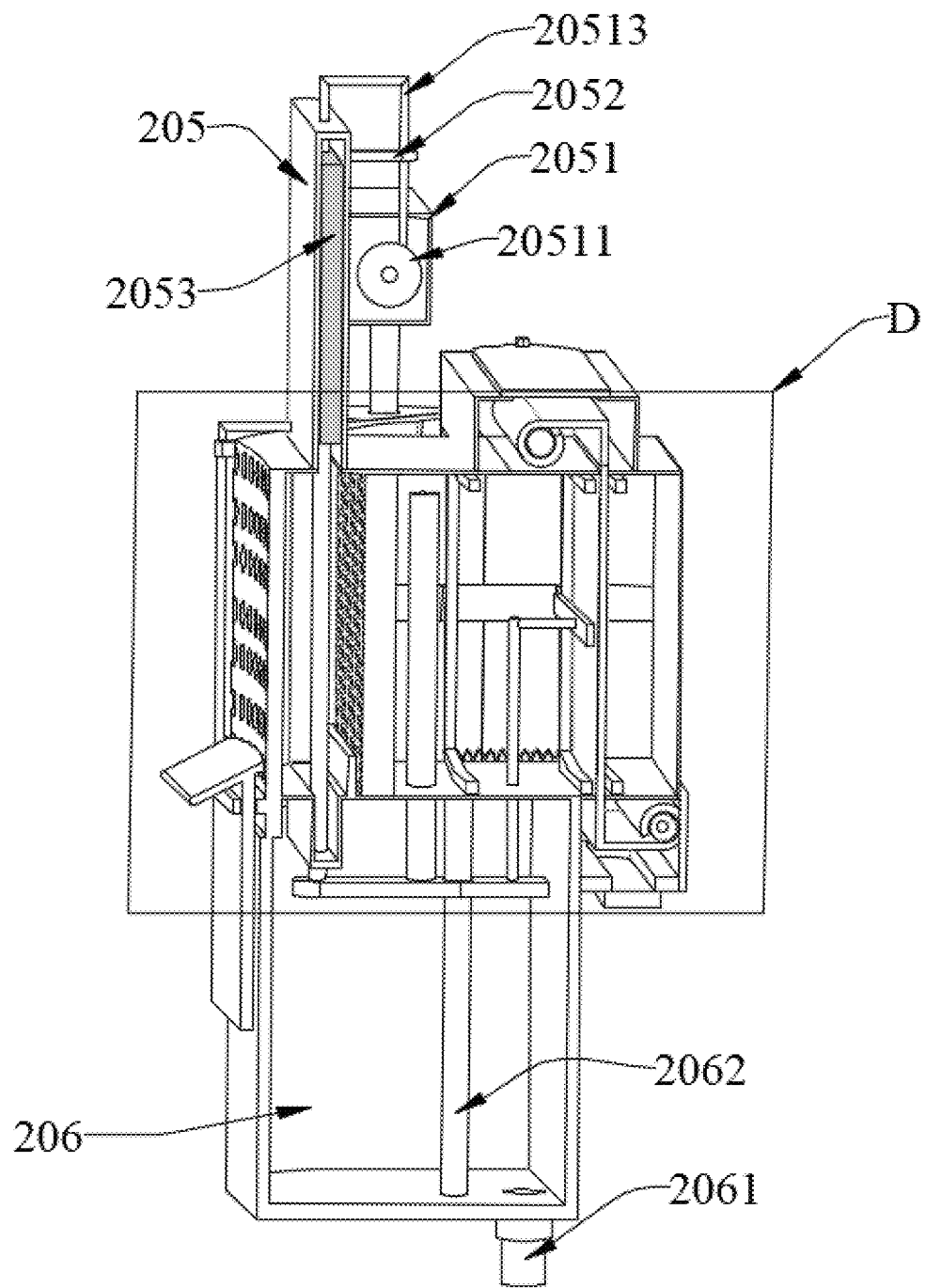
FIG. 13 is a connection schematic diagram of a connecting cavity of the present disclosure.
Figure 14:
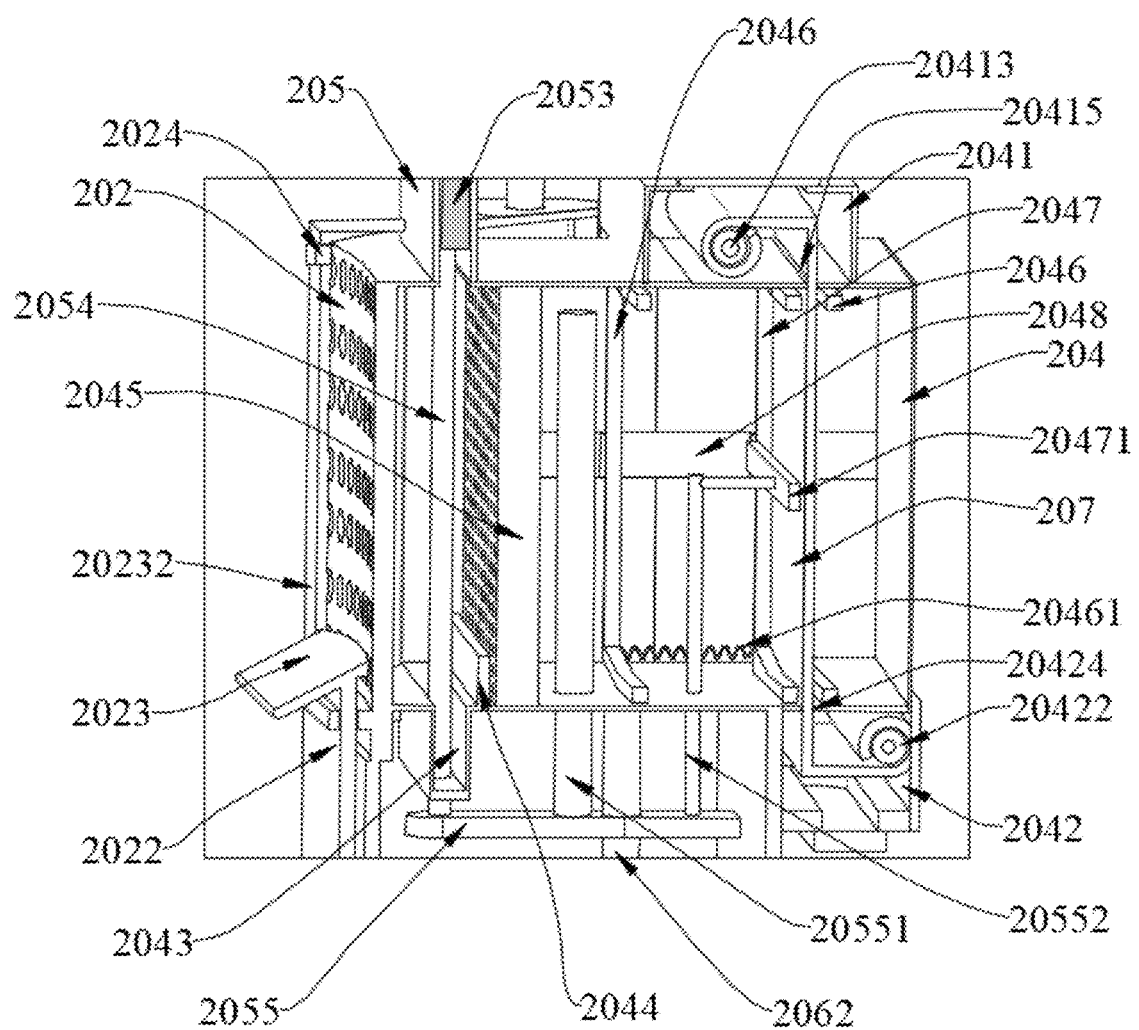
FIG. 14 shows an enlarged structure schematic diagram of part D in FIG. 13.
Figure 15:
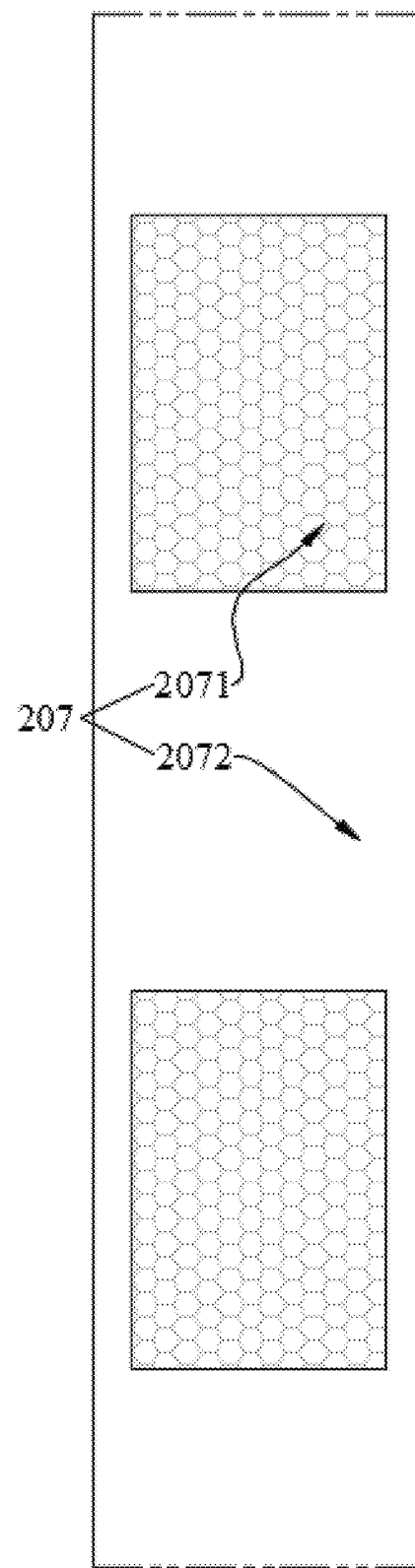
FIG. 15 is a connection schematic diagram of an adsorption layer and plastic film of the present disclosure.

LIST OF REFERENCE CHARACTERS 1. bottom fixed unit; 101. chassis; 1011. opening sleeve; 1012. counterweight block; 1013. sealing cavity;

10131. fixed driving source; 102. inserting drill bit; 1021. cavity; 10211. side groove; 10212. unfolding component; 103. control inner rope; 104. counterweight ring; 1041. control outer rope; 2. passive sampling unit; 201. ring plate; 202. filtering surface; 2021. transverse trough stripe; 2022. vertical weight plate; 2023. shovel plate; 20231. side plate; 20232. pulling rope; 2024. through block; 203. middle block; 204. connecting cavity; 2041. top roll cavity; 20411. top cover; 20412. top cavity vertical frame; 20413. top cavity roll; 20414. roll driving source; 20415. top notch; 2042. bottom roll cavity; 20421. bottom cover; 20422. output roll; 20423. output vertical frame; 20424. bottom notch; 2043. insert cavity; 2044. side baffle; 2045. diffusion layer plate; 2046. hollow fixed frame; 20461. elastic element I; 2047. hollow moving frame; 20471. transverse plate; 2048. side shift groove; 205. top vertical cavity; 2051. lateral cavity; 20511. rotating roller; 20512. rotating driving source; 20513. top pulling rope; 2052. eyeplate; 2053. counterweight sealing plate; 2054. bottom vertical rod; 2055. bottom loose plate; 20551. vertical plunger; 20552. untied and guyed rope; 206. liquid storage cavity; 2061. drain pipe; 2062. drawbar; 207. adsorption part; 2071. adsorbed layer; 2072. plastic film; 3. floating marking unit; 301. floating ring; 302. power top cavity; 3021. lower extension rod; 3022. squeezing block; 3023. lifting rope; 3024. power winding source; 30241. main drive gear; 3025. winding gear I; 30251. winding cylinder I; 3026. winding gear II; 30261. winding cylinder II; 303. storage rack; 3031. opening cylinder; 30311. elastic element II; 3032. round block; 3033. insert plate; 30331. middle groove; 304. bottom ring cavity; 3041. bottom cavity vertical frame; 3042. bottom cavity roll; 3043. bottom cavity winding source; and 305. middle rope.

DETAILED DESCRIPTION OF THE EMBODIMENTS

Embodiment 1

As shown in FIGS. 1-15, a DGT passive sampling device for water body detection includes:
- a bottom fixed unit 1, the bottom fixed unit 1 includes an inserting drill bit 102 arranged at the bottom of the bottom fixed unit, and the inserting drill bit 102 is fixed at the center of the bottom of a chassis 101;
- a passive sampling unit 2, the passive sampling unit 2 is arranged at the top of the bottom fixed unit 1, the passive sampling unit 2 includes ring plates 201 and filtering surfaces 202, the ring plate 201 is arranged at the top of the bottom fixed unit 1, a circumferential direction of the ring plate 201 is arranged with several filtering surfaces 202, an inner side of the filtering surface 202 is arranged with a diffusion layer plate 2045 and an adsorption part 207, a counterweight sealing plate 2053 is arranged between the filtering surfaces 202 and the diffusion layer plate 2045, the counterweight sealing plate 2053 is movably connected to a bottom loose plate 2055 by a bottom vertical rod 2054, the bottom loose plate 2055 is movably connected to a connecting cavity 204 by a vertical plunger 20551, and the bottom loose plate 2055 controls sliding of a hollow moving frame 2047 by an untied and guyed rope 20552; and
- a floating marking unit 3, the floating marking unit 3 is arranged at the top of the passive sampling unit 2, the floating marking unit 3 includes a winding cylinder I 30251 arranged at the top of the passive sampling unit 2, the winding cylinder I 30251 is movably connected to the chassis 101 by control inner ropes 103, the bottom of the floating marking unit 3 is arranged with a bottom ring cavity 304, the interior of the bottom ring cavity 304 is arranged with a bottom cavity winding source 3043, and the bottom cavity winding source 3043 is movably connected to passive sampling unit 2 by a middle rope 305 on the surface of a bottom cavity roll 3042.

Preferably, the chassis 101 also includes opening sleeves 1011, a circumferential direction of the top surface of the chassis 101 is arranged with several opening sleeves 1011, the interior of the opening sleeve 1011 is fixedly connected to a counterweight block 1012 by bolts, the middle part of the top surface of the chassis 101 is fixedly connected with a sealing cavity 1013, the interior of the sealing cavity 1013 is fixedly connected to a fixed driving source 10131, an output shaft of the fixed driving source 10131 runs through the chassis 101 and is movably connected to unfolding components 10212; and
- the interior of the inserting drill bit 102 is arranged with a cavity 1021, and the lateral part of the inserting drill bit 102 is arranged with a side groove 10211, the output shaft of the fixed driving source 10131 is movably connected to the side groove 10211 by the middle part of the unfolding components 10212, and a circumferential direction of the top surface of the chassis 101 is fixedly connected to several control inner ropes 103 and control outer ropes 1041.

Preferably, the floating marking unit 3 also includes a floating ring 301, the floating ring 301 preferably includes hollow rubber or plastic, and the interior of floating ring 301 is filled with air; the middle of the floating ring 301 is arranged with a power top cavity 302, and the power top cavity 302 is fixedly connected to the bottom ring cavity 304 by the floating ring 301; and
- the internal center of the power top cavity 302 is fixedly connected to a power winding source 3024, an output shaft of the power winding source 3024 is fixedly connected to a main drive gear 30241, the lateral part of the main drive gear 30241 is engaged with a winding gear I 3025, the winding gear I 3025 drives the winding cylinder I 30251 to rotatably connect to the bottom of the power top cavity 302 through a rotating shaft at the center of the winding cylinder I, and the surface of the winding cylinder I 30251 is movably connected to control inner ropes 103.

Preferably, the lateral part of the winding gear I 3025 is engaged with a winding gear II 3026, the winding gear II 3026 is rotatably connected to a winding cylinder II 30261 by a rotating shaft at the center of the winding cylinder II, the winding cylinder II 30261 is rotatably connected to the bottom surface of the power top cavity 302 by a rotating shaft, the surface of the winding cylinder II 30261 is wound with a lifting rope 3023, and the lifting rope 3023 runs through the power top cavity 302 and is movably connected to a squeezing block 3022; and
- the outer side of the bottom ring cavity 304 is fixedly connected to a lower extension rod 3021 and a storage rack 303, the storage rack 303 is arranged on the outside of lower extension rod 3021, the inner side of the storage rack 303 is arranged with several opening cylinders 3031 along a height direction of the storage rack, the interior of the opening cylinders 3031 is fixedly arranged with elastic elements II 30311, the opening cylinders 3031 are elastically connected to round blocks 3032 by the elastic elements II 30311, and the round blocks 3032 are movably connected to a counterweight ring 104 by insert plates 3033.

It is to be noted that the number of teeth of the winding gear II 3026 is a multiple of the number of teeth on the surface of the winding gear I 3025, and the multiple is preferably 5 times;

preferably, the middle of the insert plates 3033 is arranged with middle grooves 30331, the internal of the middle grooves 30331 is movably arranged with the lower extension rod 3021, the squeezing block 3022 and the lifting rope 3023, and the squeezing block 3022 is slidingly connected to the surface of the lower extension rod 3021, and the distance between the middle bottom of the slope surface and the storage rack 303 is less than the distance between the outside of the middle grooves 30331 and the storage rack 303; and the interior of the bottom ring cavity 304 is fixedly connected to a bottom cavity vertical frame 3041, the middle part of the bottom cavity vertical frame 3041 is rotatably connected to a bottom cavity roll 3042 by a rotating shaft, and the bottom cavity roll 3042 is rotatably connected to the bottom cavity winding source 3043 by a bottom cavity roll of the bottom cavity roll, and the bottom cavity winding source 3043 is fixedly connected to the surface of the bottom cavity vertical frame 3041;

the bottom of the bottom ring cavity 304 is movably connected to the control outer ropes 1041, and the surface of the control outer ropes 1041 is distributed with several counterweight rings 104, the bottom ring cavity 304 is movably connected to the chassis 101 by the control outer ropes 1041, and it is to be noted that the bottom of each counterweight ring 104 is arranged with one insert plant 3033 for limiting movement.

Operation Process:

when in use, by placing the floating marking unit 3 on the water surface, the buoyancy of the floating ring 301 suspends the floating marking unit 3 to the water surface, and then the power winding source 3024 is operated to start, making the power winding source 3024 drive the winding gear I 3025 to rotate through the main drive gear 30241 on the top of the power winding source, the winding cylinder I 30251 at the bottom of the winding gear I 3025 rotates with the winding gear I, the control inner ropes 103 on the surface of the winding cylinder I 30251 are loosened, so that the chassis 101 at the bottom of the control inner ropes 103 drops to the bottom of the water, and finally, the inserting drill bit 102 at the bottom of the chassis 101 is inserted into the underwater soils under the weight of the counterweight block 1012, while the inserting drill bit 102 is arranged in the middle of the bottom of the chassis 101 and the inserting drill bit 102 is arranged independently at the bottom of the chassis 101, thereby facilitating a smaller contact area between the inserting drill bit 102 and the underwater soils, so as to reduce the influence of underwater topography on the inserting drill bit 102 and the chassis 101, so that the inserting drill bit 102 is more stable into the underwater soils;

however, the counterweight block 1012 arranged on the outer side of the top surface of the chassis 101 can aggravate the chassis 101, so that the chassis 101 is more stable under the counterweight of the counterweight block 1012, thereby making the counterweight block 1012 and the chassis 101 move down in the water under the action of gravity; and while when the inserting drill bit 102 is inserted into the underwater soils, the fixed driving source 10131 is started at intervals, the output shaft of the fixed driving source 10131 drives the unfolding component 10212 to move outward, the unfolding component 10212 is inserted into the underwater soils, so that the inserting drill bit 102 is constrained inside the soils, thus completing the bottom anchoring of the device and improving the overall stability of the sampling device; and while when the winding gear I 3025 rotates, under the coordination of tooth ratio, the winding gear I may drive the winding gear II 3026 to rotate, making the winding cylinder II 30261 drive the lifting rope on 3023 the surface of the winding cylinder II to shrink, thereby causing the lifting rope 3023 to pull the squeezing block 3022 at the bottom of the lifting rope up along the lower extension rod 3021, so that the squeezing block 3022 may make contact with the middle grooves 30331 inside the insert plates 3033 of different heights during the upward movement, thus, when the squeezing block 3022 moves in the middle grooves 30331, the squeezing block 3022 squeezes the insert plates 3033 and the round blocks 3032 to move towards the interior of the opening cylinder 3031, the elastic elements II 30311 are squeezed, when the insert plates 3033 move towards the interior of the opening cylinder 3031, the restriction on the counterweight rings 104 at the top of the insert plates is removed, so that the counterweight rings 104 decrease in their own weight traction, while in the falling of the counterweight rings 104, the control outer ropes 1041 are stretched, so that several counterweight rings 104 are distributed at different heights at the bottom of the water, thereby making the counterweight rings 104 pull the floating marking unit 3 by the control outer ropes 1041; and the counterweight rings 104 of different heights are arranged on the outside of the control inner ropes 103, thereby reducing the instability caused by the long distance between the bottom fixed unit 1 and the floating marking unit 3.

Embodiment 2

Referring to FIGS. 1-15, this embodiment differs from the first embodiment in that:

the middle rope 305 runs through the bottom ring cavity 304 and is movably connected to a middle block 203, the middle block 203 is arranged in the middle of the ring plate 201, the outer side of the middle block 203 is fixedly connected to the connecting cavity 204, the bottom of the filtering surfaces 202 is horizontally arranged with transverse trough stripes 2021, the interior of the transverse trough stripe 2021 is movably arranged with a vertical weight plate 2022, the top of the vertical weight plate 2022 is obliquely arranged with a shovel plate 2023, the shovel plate 2023 and the filtering surfaces 202 are movably connected, the vertical weight plate 2022 is fixedly connected to the side plate 20231, and the top of the side plate 20231 is fixedly connected with a pulling rope 20232; and the surface of the filtering surfaces 202 is fixedly arranged with through blocks 2024, the top of the connecting cavity 204 is fixedly arranged with a top vertical cavity 205, the interior of the top vertical cavity 205 is movably connected to the counterweight sealing plate 2053, the pulling rope 20232 passes through the through blocks 2024 and the top vertical cavity 205 and is movably connected to the bottom of the counterweight sealing plate 2053, the counterweight sealing plate 2053 runs through the top vertical cavity 205, a lateral cavity 2051, and an eyeplate 2052 by a top pulling rope 20513 on the top of the counterweight sealing plate, then the counterweight sealing plate is movably wound to the surface of a rotating roller 20511, and the rotating roller 20511 is rotatably connected to a vertical frame through a rotating shaft in the middle of the rotating roller, the vertical frame is fixedly arranged at the interior of the lateral cavity 2051, the rotating roller 20511 is transmissibly connected to a rotating driving source 20512 through the rotating shaft in the middle of the rotating roller, the eyeplate 2052 is fixedly connected to the surface of the top vertical cavity 205, and the rotating driving source 20512 is fixedly connected to the inner wall of the lateral cavity 2051.

Preferably, the part at the bottom of the connecting cavity 204 corresponding to the counterweight sealing plate 2053 is arranged with an insert cavity 2043, the lateral part of the insert cavity 2043 is fixedly connected to a side baffle 2044, the lateral part of the side baffle 2044 is fixedly arranged with the diffusion layer plate 2045, the bottom of the connecting cavity 204 is fixedly connected to a liquid storage cavity 206, the bottom of the liquid storage cavity 206 is arranged with a drainage pipe 2061, and the middle of the drainage pipe 2061 is arranged with a ball valve, the interior of the liquid storage cavity 206 is vertically fixed with a drawbar 2062, the bottom of the counterweight sealing plate 2053 is fixedly connected to a bottom vertical rod 2054, the bottom vertical rod 2054 runs through the insert cavity 2043 and is movably connected to the bottom loose plate 2055, and the bottom loose plate 2055 is movably arranged on the surface of the drawbar 2062; and the bottom surface of the connecting cavity 204 is provided with through holes, the interior of the through holes is movably connected with the vertical plunger 20551, and the vertical plunger 20551 is fixedly connected to the surface of the bottom loose plate 2055.

It should be noted that when the bottom surface of the counterweight sealing plate 2053 is parallel to the top surface of the side baffle 2044, the vertical plunger 20551 does not pull out the bottom of the connecting cavity 204, thereby preventing the water flow outside the filtering surfaces 202 from flowing through the filtering surfaces 202 into the interior of the liquid storage cavity 206.

Preferably, the top surface of the bottom loose plate 2055 is fixedly connected to the untied and guyed rope 20552, the untied and guyed rope 20552 runs through the connecting cavity 204 and is movably connected to the transverse plate 20471, the transverse plate 20471 is fixedly connected to the hollow moving frame 2047, the inner wall of the connecting cavity 204 is transversely arranged with a side shift groove 2048, the hollow moving frame 2047 is slidingly connected to the side shift groove 2048 by a side block, hollow fixed frames 2046 are arranged on the left and right sides of the side shift groove 2048, and the hollow fixed frame 2046 is fixedly connected to the inner wall of the connecting cavity 204; and an elastic element I 20461 is arranged between the left-side hollow fixed frame 2046 and the hollow moving frame 2047, a top notch 20415 and a bottom notch 20424 are respectively arranged at the upper part and the lower part of the connecting cavity 204 corresponding to the hollow moving frame 2047, and an adsorption part 207 is movably arranged between the hollow moving frame 2047 and the right-side hollow fixed frame 2046.

It should be noted that the volume of the liquid storage cavity 206 is a multiple of the internal volume of the connecting cavity 204, and the multiple is preferably 5 times.

Preferably, a bottom roll cavity 2042 is arranged at the bottom of the connecting cavity 204, the bottom of the bottom roll cavity 2042 is arranged with a bottom cover 20421 for maintenance, the bottom cover 20421 and the bottom roll cavity 2042 are fixed by bolts, the bottom roll cavity 2042 is rotatably connected to an output roll 20422 by an output vertical frame 20423, and the surface of the output roll 20422 is movably wound with the adsorption part 207;

the top of the connecting cavity 204 is fixedly connected with a top roll cavity 2041, the top surface of the top roll cavity 2041 is fixedly connected to a top cover 20411, the top roll cavity 2041 is rotatably connected to a top cavity roll 20413 by a top cavity vertical frame 20412, the top cavity roll 20413 passes through the top cavity vertical frame 20412 by a rotating shaft in the middle of the top cavity roll and is transmissibly connected to a roll driving source 20414, and the roll driving source 20414 is fixed arranged on the inner wall of top roll cavity 2041;

the output roll 20422 passes through the bottom notch 20424, between the hollow fixed frame 2046 and the hollow moving frame 2047, and the top notch 20415 through the adsorption part 207 on the surface of output roll, and then the output roll 20422 1 is wound on the surface of the top cavity roll 20413; and the adsorption part 207 includes adsorption layers 2071 and plastic film 2072, the adsorption layers 2071 are arranged in the middle of the plastic film 2072, and the plastic film 2072 is arranged between the adjacent adsorption layers 2071, and the area of the plastic film 2072 between the adjacent adsorption layers 2071 is larger than the area of the adsorption layers 2071.

It should be noted that the fixed driving source 10131 is preferably an electric telescopic rod and is controlled by a unified PLC circuit board and powered by an external battery pack, the PLC circuit board and the external battery pack are arranged at the interior of the power top cavity 302, the power top cavity 302 and the sealing cavity 1013 are connected by wires, and the roll driving source 20414, the rotating driving source 20512, the power winding source 3024 and the bottom cavity winding source 3043 are preferably servo motors and are controlled by a unified PLC circuit board and powered by an external battery pack; the elastic element I 20461 and the elastic element II 30311 are preferred as springs, the filtering surface 202 preferably include polycarbonate material, the diffusion layer plate 2045 preferably includes agarose gel material, the adsorption layer 2071 preferably include ion exchange resin material, and the counterweight block 1012 is preferably stainless steel; and by attaching rubber layers to the surface of the output shaft of the fixed driving source 10131, the surface of the lifting rope 3023, the surface of the control inner ropes 103, the surface of the middle rope 305, the surface of the pulling rope 20232, the surface of the bottom vertical rod 2054, the surface of the vertical plunger 20551, the upper and lower surfaces of the hollow fixed frame 2046, and the surface of the untied and guyed rope 20552, the sealing performance of the movement may be improved. The rest of the structures are the same as Embodiment 1.

Operation Process:

after the inserting drill bit 102 is inserted into the underwater soils, the bottom cavity winding source 3043 is started, so that the bottom cavity winding source 3043 drives the bottom cavity roll 3042 to rotate, the rotation of the bottom cavity roll 3042 releases the downward movement of the middle ropes 305, so that the passive sampling unit 2 falls, while the bottom cavity roll 3042 may make the passive sampling unit 2 regularly distributed at different heights of the water bottom by releasing different lengths of the middle ropes 305, so that the passive sampling unit 2 may sample the water layer at different heights;

when the passive sampling unit 2 samples the water layers, the filtering surfaces 202 distributed at different directions of the floating marking unit 3 may make filtered water pass through the diffusion layer board 2045 on the back, then the filtered water is adsorbed into the adsorption layers 2071 on the surface of the adsorption part 207 between the hollow fixed frame 2046 and the hollow moving frame 2047, while when timing samplings of the passive sampling unit 2 are completed, the middle ropes 305 continue to be released, so that the passive sampling unit 2 continues to move down, when the passive sampling unit 2 moves down to the next sampling point, the rotating driving source 20512 rotates, the rotating roll 20511 rotates, making the top pulling rope 20513 on the surface of the rotating roller 20511 be released, thereby making the counterweight sealing plate 2053 constrained by the top pulling rope 20513 be released from the interior of the top vertical cavity 205 and eventually fall into the interior of the insert cavity 2043; and the filtering surfaces 202 are sealed and blocked, and the falling of the counterweight seal plate 2053 may pull the pulling rope 20232 to contract, thereby making the vertical weight plate 2022 and the shovel plate 2023 with a weight less than the counterweight sealing plate 2053 raise, so that the shovel plate 2023 lifts up the surface of the filtering surfaces 202, and the biofilm on the surface of the filtering surfaces 202 is removed;

in the downward movement of the counterweight sealing plate 2053, the counterweight sealing plate 2053 squeezes the bottom loose plate 2055 down through the bottom vertical rod 2054, so that the bottom loose plate 2055 moves down and moves along the vertical plunger 20551, so that the vertical plunger 20551 is pulled out from the bottom of the connecting cavity 204, the through holes on the bottom surface of the connecting cavity 204 sealed by the vertical plunger 20551 are opened, the water at the interior of the connecting cavity 204 is discharged into the interior of the liquid storage cavity 206 through the through holes, thereby increasing the weight of the passive sampling unit 2, and thereby reducing the accidental shaking of the passive sampling unit 2 caused by the impact of water flow in the water flow, and meanwhile, it also facilitates reducing the impact of water samples of different heights on the adsorption layers 2071 in subsequent sampling;

the moving down of the bottom loose plate 2055 may also pull the untied and guyed rope 20552 down, the untied and guyed rope 20552 pulls the transverse plate 20471 and the hollow fixed frame 2046 to close to the diffusion layer plate 2045, so that the hollow moving frame 2047 releases the clamping of the adsorption part 207 under the elastic push of the elastic element I 20461 and the closure of the hollow fixed frame 2046, it should be noted that the hollow moving frame 2047 may move between the top notch 20415 and the bottom notch 20424 when the hollow moving frame 2047 cooperates with the hollow fixed frame 2046 to clamp the adsorption part 207 under the elastic push of the elastic element I 20461, to seal the top notch 20415 and the bottom notch 20424;

after the hollow moving frame 2047 releases the clamping of the adsorption part 207, the roll driving source 20414 rotates to drive the top cavity roll 20413 to contract, so that the adsorption part 207 is rolled to the surface of the top cavity roll 20413, so that the adsorption layers 2071 on the surface of the adsorption part 207 between the hollow fixed frame 2046 and the hollow moving frame 2047 are rolled up to the surface of the top cavity roll 20413, the adsorption layers 2071 below the adsorption layers 2071 that are not transferred to the interior of the connecting cavity 204 are transferred between the hollow fixed frame 2046 and the hollow moving frame 2047, at this time, after the rotating driving source 20512 is reversed, the counterweight sealing plate 2053 makes the rotating driving source 20512 roll the top pulling rope 20513 through the rotating roller 20511, the counterweight sealing plate 2053 is rolled up to the interior of the top vertical cavity 205, at this time, the drawbar 2062 is lifted up to seal the through holes on the bottom surface of the connecting cavity 204, the bottom loose plate 2055 relieves the tension of the untied and guyed rope 20552, the hollow moving frame 2047 is driven by the elasticity of the elastic element I 20461, the hollow moving frame 2047 and the hollow fixed frame 2046 clamp the adsorption part 207, the unused adsorption layers 2071 on the surface of the adsorption part 207 are arranged in the middle of the hollow moving frame 2047, the adsorption layers 2071 continue to sample the next sampling height, thereby completing the sampling of water bodies at different heights; and while the reset of the counterweight sealing plate 2053 may release the pulling on the pulling rope 20232, so that the vertical weight plate 2022 may move downwards and reset under the action of gravity, however, the plastic film 2072 arranged between the adjacent adsorption layers 2071 may be in the roll of the top cavity roll 20413, making the plastic film 2072 may be rolled to the surface of the top cavity roll 20413, and the plastic film 2072 rolled onto the surface of the top cavity roll 20413 separates the sample that has been adsorbed, reducing the mutual influence between multiple sampling adsorption layers 2071.

Embodiment 3

Figure 16:
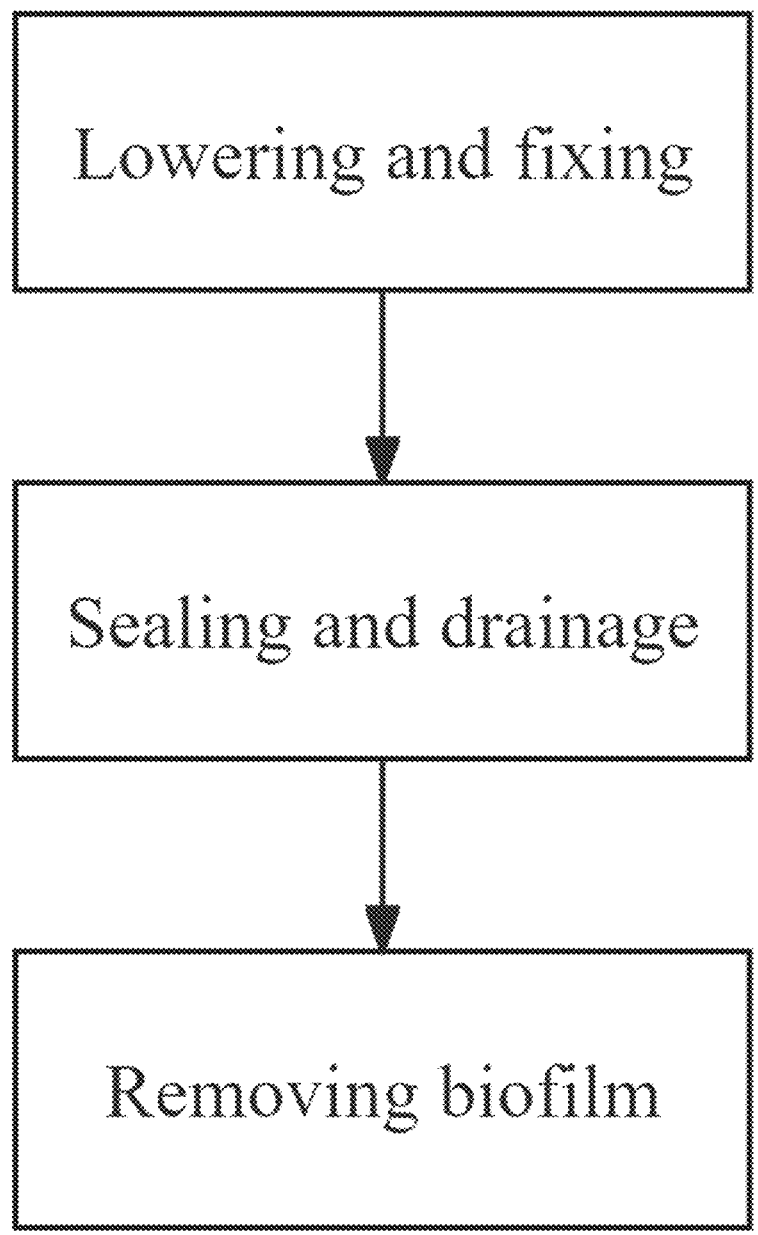
FIG. 16 is a flow diagram of a method of the present disclosure.

As shown in FIG. 16, the present embodiment provides a DGT passive sampling method for water body detection, including the following steps:

step 1: lowering and fixing: by lowering a bottom fixed unit 1 down, making an inserting drill bit 102 contact with underwater soils, and limiting movement of a chassis 101 by pulling a floating marking unit 3 through control inner ropes 103;

step 2: sealing and drainage: lowering a passive sampling unit 2 in the water bodies between the bottom fixed unit 1 and a floating marking unit 3, making the passive sampling unit 2 filter and sample water bodies by filtering surfaces 202, during the conversion sampling at different heights, a counterweight sealing plate 2053 seals the filtering surfaces 202, and opening through holes at the bottom surface of a connecting cavity 204, to make the sampling water inside the connecting cavity 204 be discharged into the interior of a liquid storage cavity 206; and step 3: removing biofilm: when the counterweight sealing plate 2053 moves down, a shovel plate 2023 may be pulled up by a pulling rope 20232, making the shovel plate 2023 clean up the surface of the filtering surfaces 202, while after the filtering surfaces are cleaned and the counterweight sealing plate 2053 is reset and unsealed, making the water bodies continue to be sampled through the filtering surfaces 202.

What is claimed is:

1. A diffusive gradients in thin-films (DGT) passive sampling device for water body detection, comprising:
    a bottom fixed unit, wherein the bottom fixed unit comprises an inserting drill bit arranged at a bottom of the bottom fixed unit, and the inserting drill bit is fixed at a center of a bottom of a chassis;
    a passive sampling unit, wherein the passive sampling unit is arranged at a top of the bottom fixed unit, the passive sampling unit comprises ring plates and a plurality of filtering surfaces, the ring plates are arranged at the top of the bottom fixed unit, a circumferential direction of the ring plates is arranged with the plurality of filtering surfaces, an inner side of the plurality of filtering surfaces is arranged with a diffusion layer plate and an adsorption part, a counterweight sealing plate is arranged between the plurality of filtering surfaces and the diffusion layer plate, the counterweight sealing plate is movably connected to a bottom loose plate by a bottom vertical rod, the bottom loose plate is movably connected to a connecting cavity by a vertical plunger, and the bottom loose plate controls sliding of a hollow moving frame by an untied and guyed rope; and
    a floating marking unit, wherein the floating marking unit is arranged at a top of the passive sampling unit, the floating marking unit comprises a first winding cylinder arranged at the top of the passive sampling unit, the first winding cylinder is movably connected to the chassis by a plurality of control inner ropes, a bottom of the floating marking unit is arranged with a bottom ring cavity, an interior of the bottom ring cavity is arranged with a bottom cavity winding source, and the bottom cavity winding source is movably connected to the passive sampling unit by a middle rope on a surface of a bottom cavity roll.

2. The DGT passive sampling device for the water body detection according to claim 1, wherein the chassis comprises a plurality of opening sleeves, a circumferential direction of a top surface of the chassis is arranged with the plurality of opening sleeves, an interior of the plurality of opening sleeves is fixedly connected to a counterweight block by bolts, a middle part of the top surface of the chassis is fixedly connected with a sealing cavity, an interior of the sealing cavity is fixedly connected to a fixed driving source, and an output shaft of the fixed driving source runs through the chassis and is movably connected to unfolding components; and
    an interior of the inserting drill bit is arranged with a cavity, and a lateral part of the inserting drill bit is arranged with a side groove, the output shaft of the fixed driving source is movably connected to the side groove by a middle part of the unfolding components, and the circumferential direction of the top surface of the chassis is fixedly connected to the plurality of control inner ropes and a plurality of control outer ropes.

3. The DGT passive sampling device for the water body detection according to claim 2, wherein the floating marking unit further comprises a floating ring, a middle of the floating ring is arranged with a power top cavity, and the power top cavity is fixedly connected to the bottom ring cavity by the floating ring; and
    an internal center of the power top cavity is fixedly connected to a power winding source, an output shaft of the power winding source is fixedly connected to a main drive gear, a lateral part of the main drive gear is engaged with a first winding gear, the first winding gear drives the first winding cylinder to rotatably connect to a bottom of the power top cavity through a first rotating shaft at a center of the first winding cylinder, and a surface of the first winding cylinder is movably wound with the plurality of control inner ropes.

4. The DGT passive sampling device for the water body detection according to claim 3, wherein a lateral part of the first winding gear is engaged with a second winding gear, the second winding gear is rotatably connected to a second winding cylinder by a second rotating shaft at a center of the second winding cylinder, the second winding cylinder is rotatably connected to a bottom surface of the power top cavity by the second rotating shaft, a surface of the second winding cylinder is wound with a lifting rope, and the lifting rope runs through the power top cavity and is movably connected to a squeezing block; and
    an outer side of the bottom ring cavity is fixedly connected to a lower extension rod and a storage rack, an inner side of the storage rack is arranged with a plurality of opening cylinders along a height direction of the storage rack, an interior of the plurality of opening cylinders is fixedly arranged with second elastic elements, the plurality of opening cylinders are elastically connected to round blocks by the second elastic elements, and the round blocks are movably connected to a plurality of counterweight rings by insert plates.

5. The DGT passive sampling device for the water body detection according to claim 4, wherein the middle rope runs through the bottom ring cavity and is movably connected to a middle block, the middle block is arranged in a middle of the ring plates, an outer side of the middle block is fixedly connected to the connecting cavity, a bottom of the plurality of filtering surfaces is horizontally arranged with transverse trough stripes, an interior of the transverse trough stripes is movably arranged with a vertical weight plate, a top of the vertical weight plate is obliquely arranged with a shovel plate, the shovel plate and the plurality of filtering surfaces are movably connected, a lateral part of the vertical weight plate is fixedly connected to a side plate, and a top of the side plate is fixedly connected with a pulling rope; and
    a surface of the plurality of filtering surfaces is fixedly arranged with through blocks, a top of the connecting cavity is fixedly arranged with a top vertical cavity, an interior of the top vertical cavity is movably connected to the counterweight sealing plate, the pulling rope passes through the through blocks and the top vertical cavity and is movably connected to a bottom of the counterweight sealing plate, the counterweight sealing plate runs through the top vertical cavity, a lateral cavity, and an eyeplate by a top pulling rope on a top of the counterweight sealing plate, then the counterweight sealing plate is movably wound to a surface of a rotating roller, and the rotating roller is transmissibly connected to a rotating driving source through a fourth rotating shaft in a middle of the rotating roller.

6. The DGT passive sampling device for the water body detection according to claim 5, wherein a part at a bottom of the connecting cavity corresponding to the counterweight sealing plate is arranged with an insert cavity, a lateral part of the insert cavity is fixedly connected to a side baffle, a lateral part of the side baffle is fixedly arranged with the diffusion layer plate, the bottom of the connecting cavity is fixedly connected to a liquid storage cavity, an interior of the liquid storage cavity is vertically fixed with a drawbar, the bottom of the counterweight sealing plate is fixedly connected to the bottom vertical rod, the bottom vertical rod runs through the insert cavity and is movably connected to the bottom loose plate, and the bottom loose plate is movably arranged on a surface of the drawbar; and a bottom surface of the connecting cavity is provided with through holes, an interior of the through holes is movably connected to the vertical plunger, and the vertical plunger is fixedly connected to a surface of the bottom loose plate.

7. The DGT passive sampling device for the water body detection according to claim 4, wherein a middle of the insert plates is arranged with middle grooves, an interior of the middle grooves is movably arranged with the lower extension rod, the squeezing block, and the lifting rope, and the squeezing block is slidingly connected to a surface of the lower extension rod;

the interior of the bottom ring cavity is fixedly connected to a bottom cavity vertical frame, a middle part of the bottom cavity vertical frame is rotatably connected to the bottom cavity roll by a third rotating shaft, and the bottom cavity roll is rotatably connected to the bottom cavity winding source by the third rotating shaft; and a bottom of the bottom ring cavity is movably connected to the plurality of control outer ropes, and a surface of the plurality of control outer ropes is distributed with the plurality of counterweight rings.

8. The DGT passive sampling device for the water body detection according to claim 7, wherein the middle rope runs through the bottom ring cavity and is movably connected to a middle block, the middle block is arranged in a middle of the ring plates, an outer side of the middle block is fixedly connected to the connecting cavity, a bottom of the plurality of filtering surfaces is horizontally arranged with transverse trough stripes, an interior of the transverse trough stripes is movably arranged with a vertical weight plate, a top of the vertical weight plate is obliquely arranged with a shovel plate, the shovel plate and the plurality of filtering surfaces are movably connected, a lateral part of the vertical weight plate is fixedly connected to a side plate, and a top of the side plate is fixedly connected with a pulling rope; and a surface of the plurality of filtering surfaces is fixedly arranged with through blocks, a top of the connecting cavity is fixedly arranged with a top vertical cavity, an interior of the top vertical cavity is movably connected to the counterweight sealing plate, the pulling rope passes through the through blocks and the top vertical cavity and is movably connected to a bottom of the counterweight sealing plate, the counterweight sealing plate runs through the top vertical cavity, a lateral cavity, and an eyeplate by a top pulling rope on a top of the counterweight sealing plate, then the counterweight sealing plate is movably wound to a surface of a rotating roller, and the rotating roller is transmissibly connected to a rotating driving source through a fourth rotating shaft in a middle of the rotating roller.

9. The DGT passive sampling device for the water body detection according to claim 8, wherein a part at a bottom of the connecting cavity corresponding to the counterweight sealing plate is arranged with an insert cavity, a lateral part of the insert cavity is fixedly connected to a side baffle, a lateral part of the side baffle is fixedly arranged with the diffusion layer plate, the bottom of the connecting cavity is fixedly connected to a liquid storage cavity, an interior of the liquid storage cavity is vertically fixed with a drawbar, the bottom of the counterweight sealing plate is fixedly connected to the bottom vertical rod, the bottom vertical rod runs through the insert cavity and is movably connected to the bottom loose plate, and the bottom loose plate is movably arranged on a surface of the drawbar; and a bottom surface of the connecting cavity is provided with through holes, an interior of the through holes is movably connected to the vertical plunger, and the vertical plunger is fixedly connected to a surface of the bottom loose plate.

10. The DGT passive sampling device for the water body detection according to claim 3, wherein the middle rope runs through the bottom ring cavity and is movably connected to a middle block, the middle block is arranged in a middle of the ring plates, an outer side of the middle block is fixedly connected to the connecting cavity, a bottom of the plurality of filtering surfaces is horizontally arranged with transverse trough stripes, an interior of the transverse trough stripes is movably arranged with a vertical weight plate, a top of the vertical weight plate is obliquely arranged with a shovel plate, the shovel plate and the plurality of filtering surfaces are movably connected, a lateral part of the vertical weight plate is fixedly connected to a side plate, and a top of the side plate is fixedly connected with a pulling rope; and a surface of the plurality of filtering surfaces is fixedly arranged with through blocks, a top of the connecting cavity is fixedly arranged with a top vertical cavity, an interior of the top vertical cavity is movably connected to the counterweight sealing plate, the pulling rope passes through the through blocks and the top vertical cavity and is movably connected to a bottom of the counterweight sealing plate, the counterweight sealing plate runs through the top vertical cavity, a lateral cavity, and an eyeplate by a top pulling rope on a top of the counterweight sealing plate, then the counterweight sealing plate is movably wound to a surface of a rotating roller, and the rotating roller is transmissibly connected to a rotating driving source through a fourth rotating shaft in a middle of the rotating roller.

11. The DGT passive sampling device for the water body detection according to claim 10, wherein a part at a bottom of the connecting cavity corresponding to the counterweight sealing plate is arranged with an insert cavity, a lateral part of the insert cavity is fixedly connected to a side baffle, a lateral part of the side baffle is fixedly arranged with the diffusion layer plate, the bottom of the connecting cavity is fixedly connected to a liquid storage cavity, an interior of the liquid storage cavity is vertically fixed with a drawbar, the bottom of the counterweight sealing plate is fixedly connected to the bottom vertical rod, the bottom vertical rod runs through the insert cavity and is movably connected to the bottom loose plate, and the bottom loose plate is movably arranged on a surface of the drawbar; and a bottom surface of the connecting cavity is provided with through holes, an interior of the through holes is movably connected to the vertical plunger, and the vertical plunger is fixedly connected to a surface of the bottom loose plate.

12. The DGT passive sampling device for the water body detection according to claim 1, wherein a top surface of the bottom loose plate is fixedly connected to the untied and guyed rope, the untied and guyed rope runs through the connecting cavity and is movably connected to a transverse plate, the transverse plate is fixedly connected to the hollow moving frame, an inner wall of the connecting cavity is transversely arranged with a side shift groove, the hollow moving frame is slidingly connected to the side shift groove by a side block, a left-side hollow fixed frame and a right-side hollow fixed frame are respectively arranged on left and right sides of the side shift groove, and the left-side hollow fixed frame and the right-side hollow fixed frame are fixedly connected to the inner wall of the connecting cavity; and a first elastic element is arranged between the left-side hollow fixed frame and the hollow moving frame, a top notch and a bottom notch are respectively arranged at an upper part and a lower part of the connecting cavity corresponding to the hollow moving frame, and the adsorption part is movably arranged between the hollow moving frame and the right-side hollow fixed frame.

13. The DGT passive sampling device for the water body detection according to claim 12, wherein a bottom roll cavity is arranged at a bottom of the connecting cavity, the bottom roll cavity is rotatably connected to an output roll by an output vertical frame, and a surface of the output roll is movably wound with the adsorption part;

a top of the connecting cavity is fixedly connected with a top roll cavity, the top roll cavity is rotatably connected to a top cavity roll by a top cavity vertical frame, and the top cavity roll passes through the top cavity vertical frame by a rotating shaft in a middle of the top cavity roll and is transmissibly connected to a roll driving source; and the adsorption part comprises adsorption layers and a plastic film, the adsorption layers are arranged in a middle of the plastic film, and the plastic film is arranged between adjacent adsorption layers, and an area of the plastic film between the adjacent adsorption layers is larger than an area of the adsorption layers.

14. A DGT passive sampling method for water body detection, using the DGT passive sampling device for the water body detection according to claim 13, and comprising the following steps:

step 1: lowering and fixing: by lowering the bottom fixed unit down, allowing the inserting drill bit to contact with underwater soils, and limiting movement of the chassis by pulling the floating marking unit through the plurality of control inner ropes;

step 2: sealing and draining: lowering the passive sampling unit in water bodies between the bottom fixed unit and the floating marking unit, allowing the passive sampling unit to filter and sample the water bodies by the plurality of filtering surfaces, during conversion sampling at different heights, sealing the plurality of filtering surfaces by the counterweight sealing plate, and opening through holes at a bottom surface of the connecting cavity, to allow sampling water inside the connecting cavity to be discharged into an interior of a liquid storage cavity; and step 3: removing biofilm: when the counterweight sealing plate moves down, pulling up a shovel plate by a pulling rope, allowing the shovel plate to clean up a surface of the plurality of filtering surfaces, while after the plurality of filtering surfaces are cleaned and the counterweight sealing plate is reset and unsealed, allowing the water bodies to continue to be sampled through the plurality of filtering surfaces.

\* \* \* \* \*